(12) United States Patent
Carbunaru et al.

(10) Patent No.: US 10,350,420 B2
(45) Date of Patent: Jul. 16, 2019

(54) EXTERNAL CHARGER WITH CUSTOMIZABLE MAGNETIC CHARGING FIELD

(71) Applicant: Boston Scientific Neuromodulation Corporation, Valencia, CA (US)

(72) Inventors: Rafael Carbunaru, Valley Village, CA (US); Andrew DiGiore, San Francisco, CA (US); Todd Whitehurst, Frederick, MD (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 57 days.

(21) Appl. No.: 15/615,350

(22) Filed: Jun. 6, 2017

(65) Prior Publication Data
US 2017/0281956 A1 Oct. 5, 2017

Related U.S. Application Data

(63) Continuation of application No. 13/099,906, filed on May 3, 2011, now Pat. No. 9,700,730.
(Continued)

(51) Int. Cl.
*A61N 1/08* (2006.01)
*A61N 1/372* (2006.01)
*A61N 1/378* (2006.01)

(52) U.S. Cl.
CPC ....... *A61N 1/37229* (2013.01); *A61N 1/3787* (2013.01); *A61N 1/08* (2013.01);
(Continued)

(58) Field of Classification Search
CPC .... A61N 1/37229; A61N 1/3787; A61N 1/08; A61N 1/37205; A61N 1/37211; A61N 1/378
See application file for complete search history.

(56) References Cited

U.S. PATENT DOCUMENTS 5,995,874 A * 11/1999 Borza .................. A61N 1/3787
607/61
6,208,235 B1 3/2001 Trontelj
(Continued)

FOREIGN PATENT DOCUMENTS

WO 2006/010013 1/2006

*Primary Examiner* — Lindsey G Wehrheim
(74) *Attorney, Agent, or Firm* — Lewis & Reese, PLLC

(57) ABSTRACT

Improved external chargers for charging an implantable medical device, and particularly useful in charging a plurality of such devices, are disclosed. Each of the various embodiments include a plurality of field customization coils for customizing the magnetic charging field generated by the external charger such that the magnetic charging field is not radially symmetric. For example, one embodiment includes a primary coil with a plurality of field customization coils distributed radially with respect to the coil. The generated magnetic charging field can be rendered radially asymmetric by selectively activating or disabling the field customization coils in response to data quantifying the coupling between the various implants and the field customization coils in the charger. If there is a relatively high coupling between a particular implant and a particular customization coil for example, that customization coil can be activated to counter the magnetic charging field at that location, while still maintaining a relatively high magnetic charging field at the location of other implants that may have lower couplings.

20 Claims, 34 Drawing Sheets

Related U.S. Application Data

(60) Provisional application No. 61/332,555, filed on May 7, 2010.

(52) U.S. Cl.
CPC .......... *A61N 1/378* (2013.01); *A61N 1/37205* (2013.01); *A61N 1/37211* (2013.01)

(56) References Cited

U.S. PATENT DOCUMENTS

| | | |
|---|---|---|
| 6,463,329 B1 | 10/2002 | Goedeke |
| 6,663,556 B2 | 12/2003 | Barker |
| 7,389,140 B1 | 6/2008 | Kroll |
| 2005/0288742 A1* | 12/2005 | Giordano ............ A61N 1/3787 607/61 |
| 2008/0172109 A1 | 7/2008 | Rahman et al. |
| 2009/0069869 A1 | 3/2009 | Stouffer et al. |
| 2009/0112291 A1 | 4/2009 | Wahlstrand et al. |
| 2010/0204756 A1 | 8/2010 | Aghassian |
| 2011/0004278 A1 | 1/2011 | Aghassian et al. |
| 2011/0093048 A1 | 4/2011 | Aghassian |
| 2011/0121777 A1 | 5/2011 | Carbunaru |
| 2011/0163714 A1 | 7/2011 | Ettes |

* cited by examiner

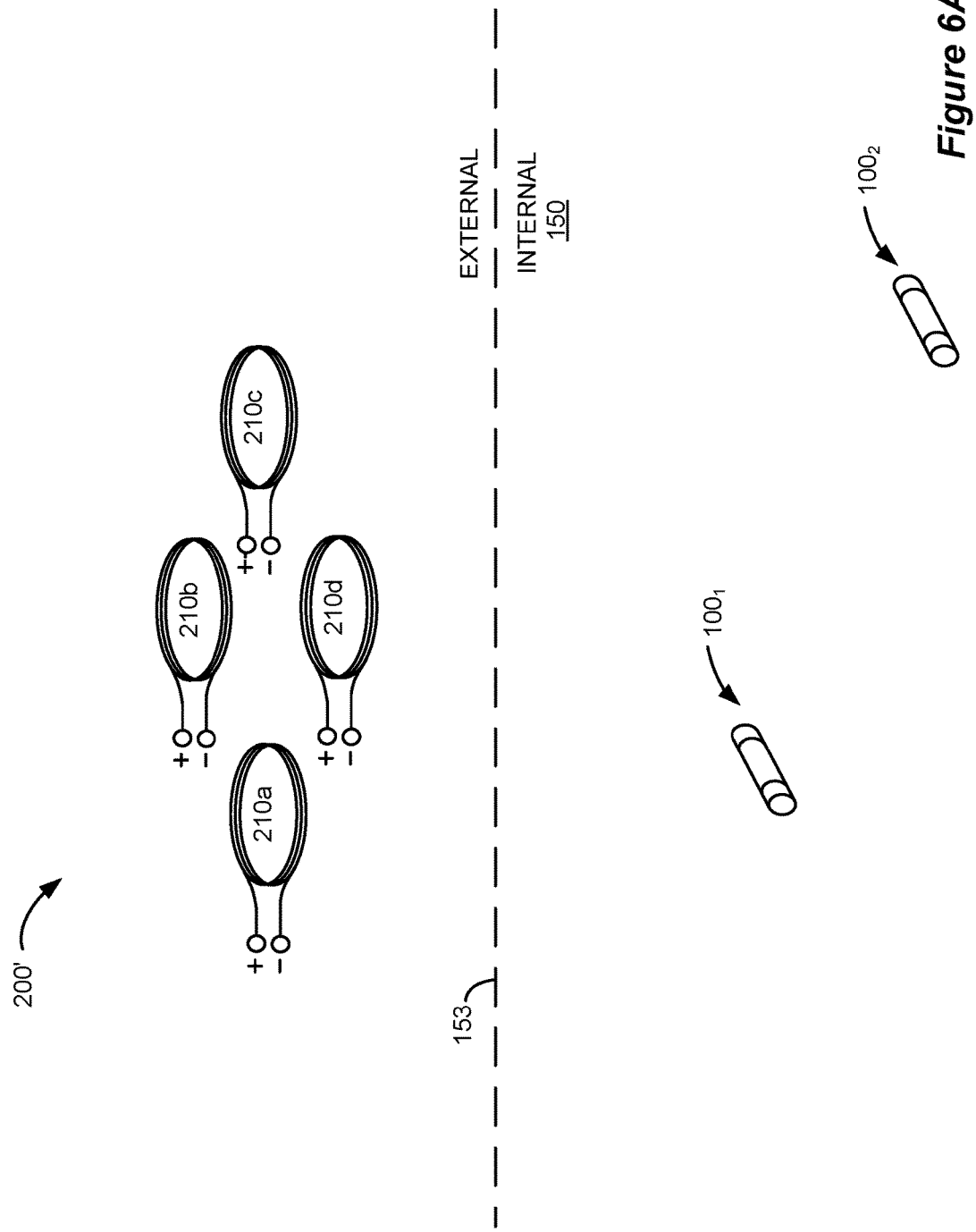

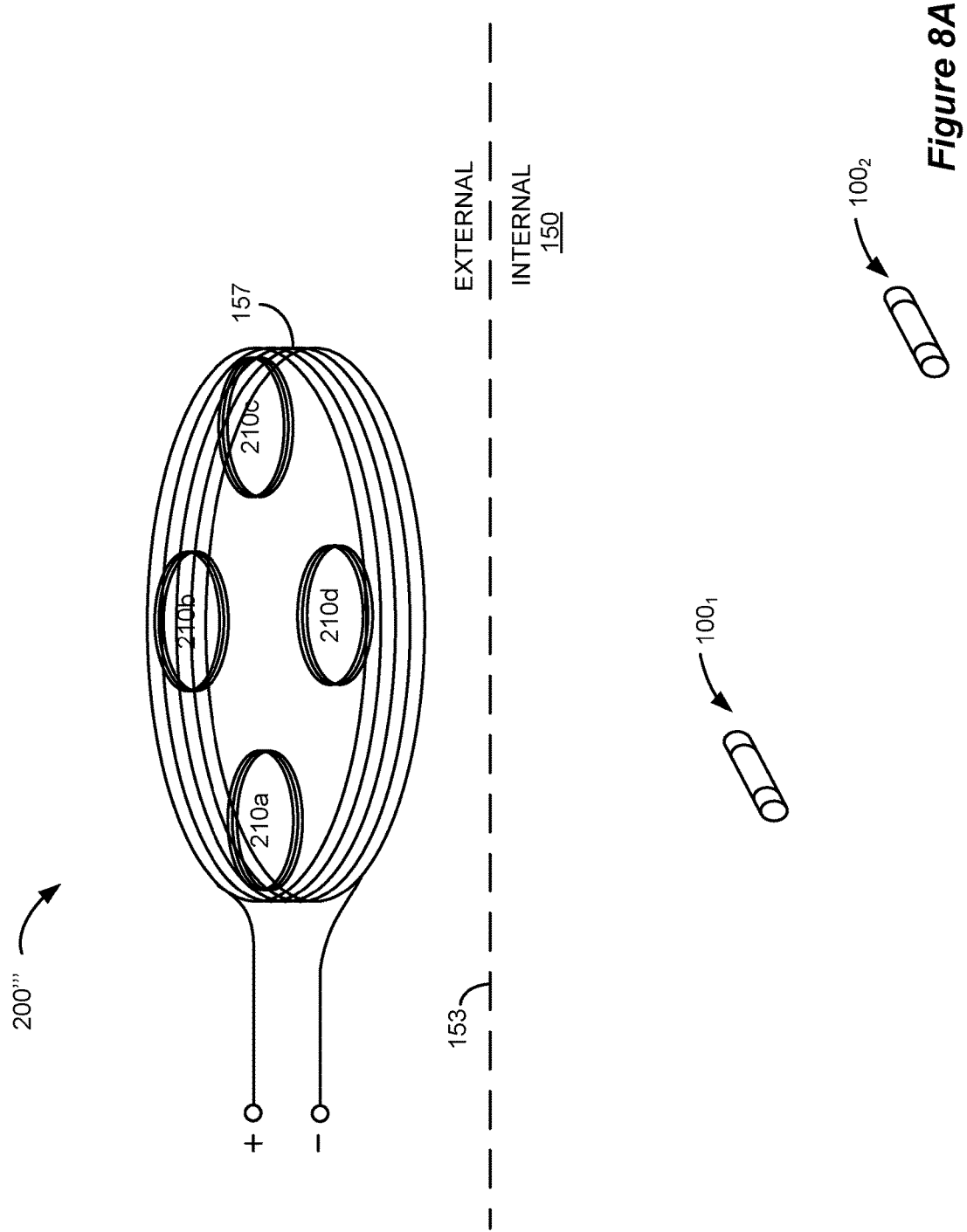

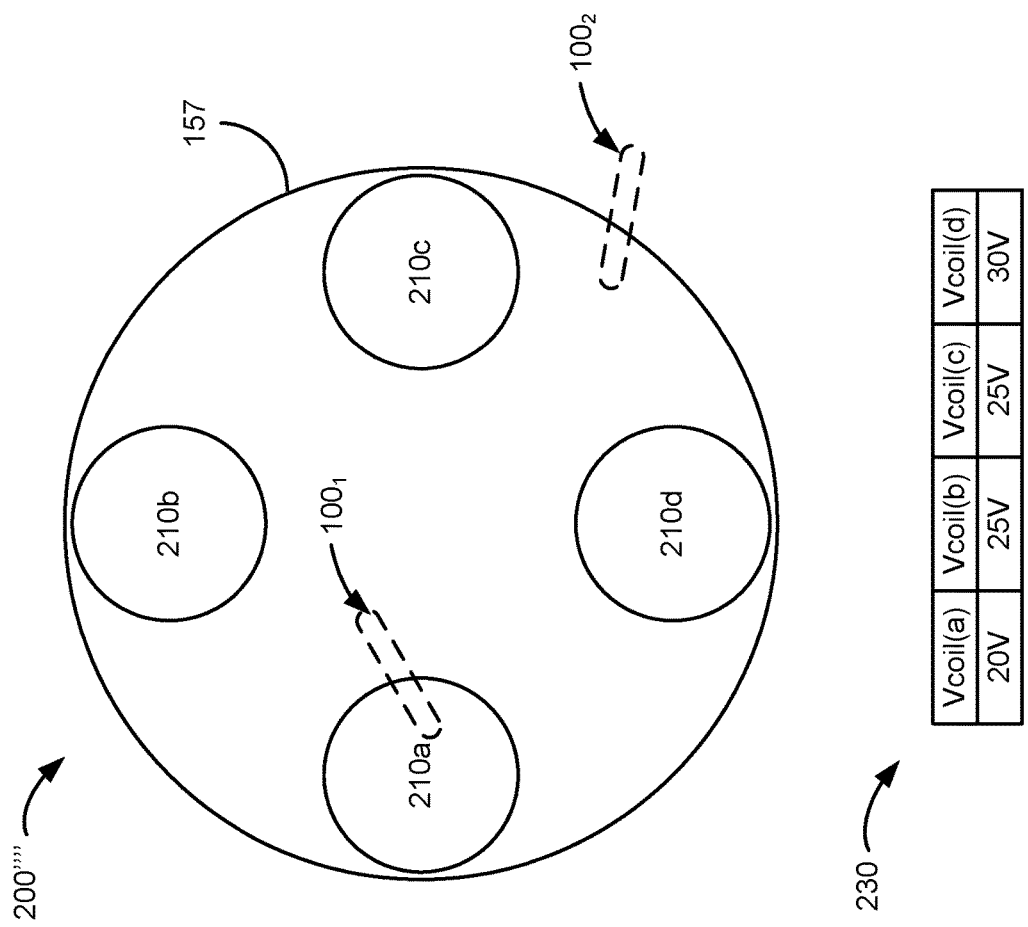

EXTERNAL CHARGER WITH CUSTOMIZABLE MAGNETIC CHARGING FIELD

CROSS REFERENCE TO RELATED APPLICATIONS

This is a continuation of U.S. patent application Ser. No. 13/099,906, filed May 3, 2011, which is a non-provisional of U.S. Provisional Application Ser. No. 61/332,555, filed May 7, 2010. Priority is claimed to these applications, and they are incorporated herein by reference in their entireties.

FIELD OF THE INVENTION

The present invention relates generally to an external charger used to inductively charge a plurality of implantable medical devices such as neurostimulators.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder subluxation, etc. The present invention may find applicability in all such applications and in other implantable medical device systems, although the description that follows will generally focus on the use of the invention in a microstimulator device system of the type disclosed in U.S. patent application Ser. No. 12/425,505, filed Apr. 17, 2009.

Microstimulator devices typically comprise a small, generally-cylindrical housing which carries electrodes for producing a desired stimulation current. Devices of this type are implanted proximate to the target tissue to allow the stimulation current to stimulate the target tissue to provide therapy for a wide variety of conditions and disorders. A microstimulator usually includes or carries stimulating electrodes intended to contact the patient's tissue, but may also have electrodes coupled to the body of the device via a lead or leads. A microstimulator may have two or more electrodes. Microstimulators benefit from simplicity. Because of their small size, the microstimulator can be directly implanted at a site requiring patient therapy.

FIG. 1 illustrates an exemplary implantable microstimulator 100. As shown, the microstimulator 100 includes a power source 145 such as a battery, a programmable memory 146, electrical circuitry 144, and a coil 147. These components are housed within a capsule 202, which is usually a thin, elongated cylinder, but may also be any other shape as determined by the structure of the desired target tissue, the method of implantation, the size and location of the power source 145, and/or the number and arrangement of external electrodes 142. In some embodiments, the volume of the capsule 202 is substantially equal to or less than three cubic centimeters.

The battery 145 supplies power to the various components within the microstimulator 100, such the electrical circuitry 144 and the coil 147. The battery 145 also provides power for therapeutic stimulation current sourced or sunk from the electrodes 142. The power source 145 may be a primary battery, a rechargeable battery, a capacitor, or any other suitable power source. Systems and methods for charging a rechargeable battery 145 will be described further below.

The coil 147 is configured to receive and/or emit a magnetic field that is used to communicate with, or receive power from, one or more external devices that support the implanted microstimulator 100, examples of which will be described below. Such communication and/or power transfer may be transcutaneous as is well known.

The programmable memory 146 is used at least in part for storing one or more sets of data, including electrical stimulation parameters that are safe and efficacious for a particular medical condition and/or for a particular patient. Electrical stimulation parameters control various parameters of the stimulation current applied to a target tissue including the frequency, pulse width, amplitude, burst pattern (e.g., burst on time and burst off time), duty cycle or burst repeat interval, ramp on time and ramp off time of the stimulation current, etc.

The illustrated microstimulator 100 includes electrodes 142-1 and 142-2 on the exterior of the capsule 202. The electrodes 142 may be disposed at either end of the capsule 202 as illustrated, or placed along the length of the capsule. There may also be more than two electrodes arranged in an array along the length of the capsule. One of the electrodes 142 may be designated as a stimulating electrode, with the other acting as an indifferent electrode (reference node) used to complete a stimulation circuit, producing monopolar stimulation. Or, one electrode may act as a cathode while the other acts as an anode, producing bipolar stimulation. Electrodes 142 may alternatively be located at the ends of short, flexible leads. The use of such leads permits, among other things, electrical stimulation to be directed to targeted tissue(s) a short distance from the surgical fixation of the bulk of the device 100.

The electrical circuitry 144 produces the electrical stimulation pulses that are delivered to the target nerve via the electrodes 142. The electrical circuitry 144 may include one or more microprocessors or microcontrollers configured to decode stimulation parameters from memory 146 and generate the corresponding stimulation pulses. The electrical circuitry 144 will generally also include other circuitry such as the current source circuitry, the transmission and receiver circuitry coupled to coil 147, electrode output capacitors, etc.

The external surfaces of the microstimulator 100 are preferably composed of biocompatible materials. For example, the capsule 202 may be made of glass, ceramic, metal, or any other material that provides a hermetic package that excludes water but permits passage of the magnetic fields used to transmit data and/or power. The electrodes 142 may be made of a noble or refractory metal or compound, such as platinum, iridium, tantalum, titanium, titanium nitride, niobium or alloys of any of these, to avoid corrosion or electrolysis which could damage the surrounding tissues and the device.

The microstimulator 100 may also include one or more infusion outlets 201, which facilitate the infusion of one or more drugs into the target tissue. Alternatively, catheters may be coupled to the infusion outlets 201 to deliver the drug therapy to target tissue some distance from the body of the microstimulator 100. If the microstimulator 100 is configured to provide a drug stimulation using infusion outlets 201, the microstimulator 100 may also include a pump 149 that is configured to store and dispense the one or more drugs.

Turning to FIG. 2, the microstimulator 100 is illustrated as implanted in a patient 150, and further shown are various external components that may be used to support the implanted microstimulator 100. An external controller 155 may be used to program and test the microstimulator 100 via communication link 156. Such link 156 is generally a two-way link, such that the microstimulator 100 can report its status or various other parameters to the external controller 155. Communication on link 156 occurs via magnetic inductive coupling. Thus, when data is to be sent from the external controller 155 to the microstimulator 100, a coil 158 in the external controller 155 is excited to produce a magnetic field that comprises the link 156, which magnetic field is detected at the coil 147 in the microstimulator. Likewise, when data is to be sent from the microstimulator 100 to the external controller 155, the coil 147 is excited to produce a magnetic field that comprises the link 156, which magnetic field is detected at the coil 158 in the external controller. Typically, the magnetic field is modulated, for example with Frequency Shift Keying (FSK) modulation or the like, to encode the data.

An external charger 151 provides power used to recharge the battery 145 (FIG. 1). Such power transfer occurs by energizing the coil 157 in the external charger 151, which produces a magnetic field comprising link 152. This magnetic field 152 energizes the coil 147 through the patient 150's tissue, and which is rectified, filtered, and used to recharge the battery 145 as explained further below. Link 152, like link 156, can be bidirectional to allow the microstimulator 100 to report status information back to the external charger 151. For example, once the circuitry 144 in the microstimulator 100 detects that the power source 145 is fully charged, the coil 147 can signal that fact back to the external charger 151 so that charging can cease. Charging can occur at convenient intervals for the patient 150, such as every night.

FIGS. 3A and 3B illustrate salient portions of the microstimulator's power circuitry 160. When the coil 157 in the external charger 151 is stimulated by AC current Iprim, a magnetic charging field 161 is produced. This field 161 (comprising part of link 152) is received at coil 147 in the microstimulator 100. The coil 147 in combination with capacitor 162 comprises a resonant circuit, or tank circuit, which produces an AC voltage at Va. This AC voltage is rectified by rectifier circuitry 164, which can comprise a well-known four-diode bridge circuit, although it is shown in FIG. 3B as a single diode for simplicity. Capacitor 166 assists to filter the signal at node Vb, such that Vb is essentially a DC voltage, although perhaps having a negligible ripple. Intervening between Vb and the rechargeable battery 145 is charging circuitry 170, which ultimately takes the DC voltage Vb and uses it to produce a controlled battery charging current, Ibat. Charging circuitry 170 is well known. One skilled in the art will recognize that the power circuitry 160 may include other components not shown for simplicity.

Depending on the patient's condition, it may be desirable to implant more than one microstimulator to provide more complex stimulation to the patient and/or to provide stimulation in different locations. For instance, as shown in the example of FIG. 4, a first microstimulator $100_1$ is implanted at a first location, and a second microstimulator $100_2$ is implanted at a second location. Additional microstimulators could also be implanted if more complicated therapies are indicated, but only two microstimulators are shown in FIG. 4 for simplicity. Microstimulators $100_1$ and $100_2$ may operate independently or may operate in a coordinated manner.

The external controller 155 can communicate with each microstimulator independently, with communications accompanied by a header containing an address of the microstimulator. Such addressing ensures no confusion when communicating with the two microstimulators $100_1$ and $100_2$, and thus allows each to be independently programmed and monitored by the external controller 155. Such addressing also allows the two microstimulators $100_1$ and $100_2$ to communicate with each other.

Both microstimulators $100_1$ and $100_2$ will eventually need to have their batteries recharged using external charger 151, and such charging presents special challenges. Each of the microstimulators $100_1$ and $100_2$ could be charged independently, but this would take additional time. Even if a patient had only two microstimulators implanted, the total time to charge both would roughly double compared to a single implant, which would comprise a major inconvenience to the patient. Independent charging of the microstimulators also requires some coordination between the microstimulators $100_1$ and $100_2$. For example, the microcontrollers $100_1$ and $100_2$ would have to know when to enable or disable charging by opening or connecting their coils 147.

Because of such issues, the inventors consider it preferable to charge both microstimulators $100_1$ and $100_2$ at the same time. However, while this approach would provide for faster charging, it is a challenge to optimize and to do so safely. Of particular concern is implant heating, which one skilled in the art will understand is an inevitable side effect of charging using magnetic fields. Heating can result from several different sources, such as eddy currents in conductive portions of the implant, or heating of the various components in the power circuitry 160. Implant heating is a serious safety concern; if an implant exceeds a given safe temperature (e.g., 41° C.), the tissue surrounding the implant may be aggravated or damaged.

Generally speaking, implant heating is a function of both the strength of the magnetic charging field, and the coupling between the external charger 151 and the implant. The strength of the magnetic charging field can be increased by increasing the excitation current, Iprim, in the coil 157 of the external charger 151. Increasing the magnetic charging field will increase the current/voltage induced in the coil 147 of the microstimulator 100, which increases the battery charging current, Ibat (FIG. 3B). Increasing the battery charging current speeds up charging, but also increases heat dissipation in the device.

Coupling between the external charger 151 and the implant affects how readily the magnetic charging field is passed to the implant, i.e., how strongly the effect of the magnetic charging field is felt at the implant. Many factors affecting coupling, such as the inductances of the coil 157 in the external charger 151 and the coil 147 in the implant; alignment, angle and distance between the coils 151 and 147; the permittivity of any materials (e.g., tissue, air) between the coils, etc. Coupling between an external charger and an implant is discussed further in U.S. patent application Ser. No. 12/498,049, filed Jul. 6, 2009. Generally speaking, if the coupling between the coils is relatively high, a relatively large current/voltage will be induced in implant coil 147, leading to faster charging and higher power dissipation (higher temperatures) in the implant.

Because of differences in the placement of multiple microstimulators in a patient, one could expect that the coupling between the external charger 151 and each of those microstimulators would differ. This means that the same magnetic charging field produced by the external charger 151 would result in different amounts of power dissipation in each of the microstimulators. Consider FIG. 4: microstimulator $100_2$ is located deeper in the patient, and is therefore farther away from the external charger 151 than is microstimulator $100_1$. Moreover, the angle θ between the coil 147 in microstimulator $100_2$ and coil 157 in external charger 151 is relatively large, and the offset of their axes D is relatively large. These factors all contribute to low coupling between the external charger 157 and microstimulator $100_2$ as compared to microstimulator $100_1$.

As a result, when the external charger 151 produces a magnetic charging field, microstimulator $100_1$ will charge more quickly—and will generate more heat—than will microstimulator $100_2$. As noted, this makes optimization difficult. If the generated magnetic charging field is optimized to charge microstimulator $100_2$ as quickly as possible at a safe temperature, then microstimulator $100_1$ would become too hot. By contrast, if the generated magnetic charging field is optimized to charge microstimulator $100_1$ as quickly as possible at a safe temperature, then microstimulator $100_2$ would charge too slowly.

BRIEF DESCRIPTION OF THE DRAWINGS

FIGS. 6A-6F illustrate the structure and operation of a second embodiment of an improved external charger particularly useful in charging a plurality of implantable medical devices, in which the charger comprises a plurality of field customization coils without a primary coil.

FIGS. 8A-8D illustrate the structure and operation of a fourth embodiment of an improved external charger particularly useful in charging a plurality of implantable medical devices, in which coupling information between the charger and the implants need not be telemetered from the implants but is instead measured at the charger.

FIGS. 9A-9C illustrate the structure and operation of a fifth embodiment of an improved external charger particularly useful in charging a plurality of implantable medical devices, in which coupling information between the charger and the implants need not be telemetered from the implants but is instead measured at the charger.

DETAILED DESCRIPTION

Improved external chargers for charging an implantable medical device, and particularly useful in charging a plurality of such devices, are disclosed. Each of the various embodiments include a plurality of field customization coils for customizing the magnetic charging field generated by the external charger such that the magnetic charging field is not radially symmetric. For example, one embodiment includes a primary coil with a plurality of field customization coils distributed radially with respect to the coil. The generated magnetic charging field can be rendered radially asymmetric by selectively activating or disabling the field customization coils in response to data quantifying the coupling between the various implants and the field customization coils in the charger. If there is a relatively high coupling between a particular implant and a particular customization coil for example, that customization coil can be activated to counter the magnetic charging field at that location, while still maintaining a relatively high magnetic charging field at the location of other implants that may have lower couplings. Customizing the magnetic field from the external charger in this fashion allows multiple implants to be charged simultaneously and more uniformly by mitigating concerns that implants having different couplings will charge at different speeds and temperatures. Customizing the magnetic field also can benefit the charging of a single implant, which is especially useful if the implant and the charger are not well aligned.

Figure 5A:
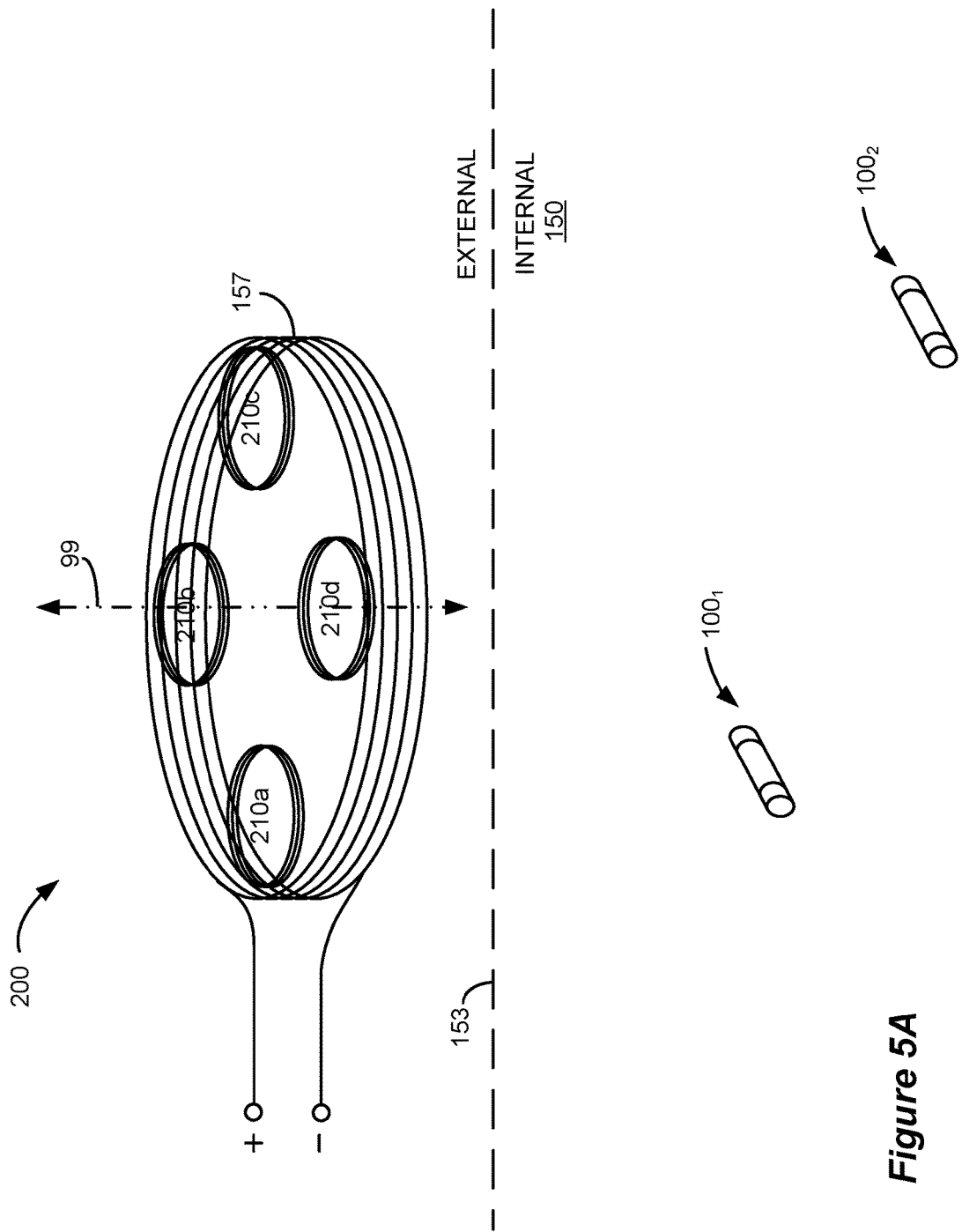
FIGS. 5A-5G illustrate the structure and operation of a first embodiment of an improved external charger particularly useful in charging a plurality of implantable medical devices, in which the charger comprises a plurality of field customization coils as well as a primary coil.

FIGS. 5A to 5G illustrate a first embodiment of an improved external charger 200. Starting with FIG. 5A, the charger 200 is shown in proximity to two microstimulators $100_1$ and $100_2$ similar to those discussed in the Background section. As seen in FIG. 5A, the housing and electrical circuitry of the external charger 200 have been removed to show primary coil 157, which was also discussed in Background. (Typical housings and other electrical circuitry for an external charger is disclosed in U.S. patent application Ser. No. 12/562,694, filed Sep. 18, 2009, which is incorporated herein by reference in its entirety). Additionally shown are four field customization coils 210a-d. The field customization coils 210a-d are distributed with radial symmetry with respect to a main axis 99 of the primary coil 157, as can also be seen in the simplified plan view of FIG. 5B. One skilled in the art appreciating the teaching of this disclosure will realize that the use of four field customization coils 210a-d is merely one example, and that other numbers of such coils could be used. Additionally, radial symmetry of the field customization coils 210a-d is not strictly required, and such coils can be arranged asymmetrically or in different locations with respect to the primary coil 157 (inside or outside the coil, etc.). The field customization coils 210a-d may be comprised of different wire from the primary charging coil 157, and may contain differing numbers of turns.

Field customization coils 210a-d operate first to determine the coupling of the various microstimulators $100_1$ and $100_2$ during a testing phase and thereafter use such coupling data to customize the magnetic charging field 201 (FIG. 5G) generated by external charger 200 during an actual charging session. Determination of coupling is first discussed. Note from FIGS. 5A and 5B that the microstimulators $100_1$ and $100_2$ are positioned differently with respect to the external charger 200: microstimulator $100_1$ is closer to the left edge of the charger 200 and is also more shallowly implanted in the patient 150; microstimulator $100_2$ is closer to the right edge of the charger 200 and is more deeply implanted in the patient 150. Additionally, and although not shown, the angle between the coils 147 in each of the microstimulators $100_1$ and $100_2$ may differ with respect to the field customization coils 210a-d in manners that would affect their couplings.

As a result of such an arrangement, each of the microstimulators $100_1$ and $100_2$ will have different degrees of coupling with each of the field customization coils $210a\text{-}d$. For example, if one ignores potential angular differences and focuses only on location, microstimulator $100_1$ will have a relatively high coupling with field customization coil $210a$ because it is relatively close to such coil $210a$. By contrast, microstimulator $100_2$ will have a relatively low coupling to coil $210a$ because it is far away.

Figure 3A:
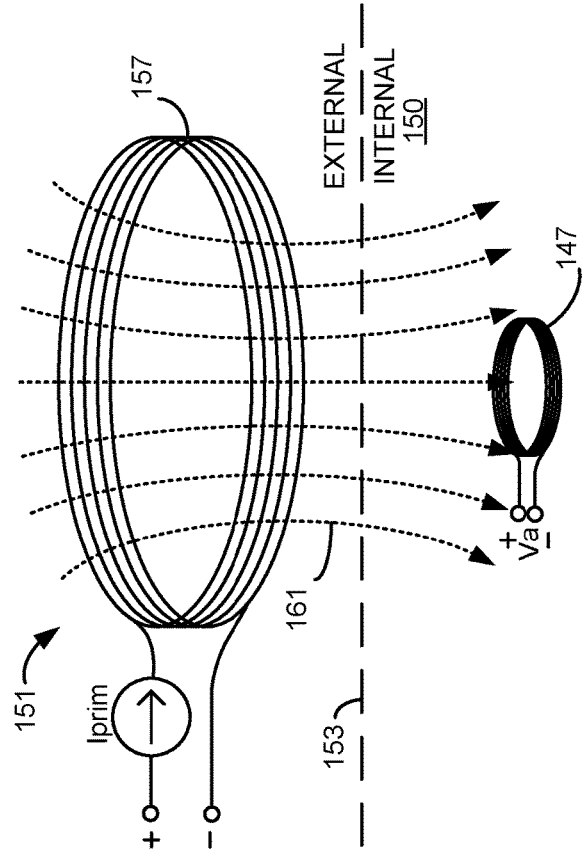
FIGS. 3A and 3B illustrates the operation of charging circuitry within the implant and external charger, in accordance with the prior art.
Figure 3B:
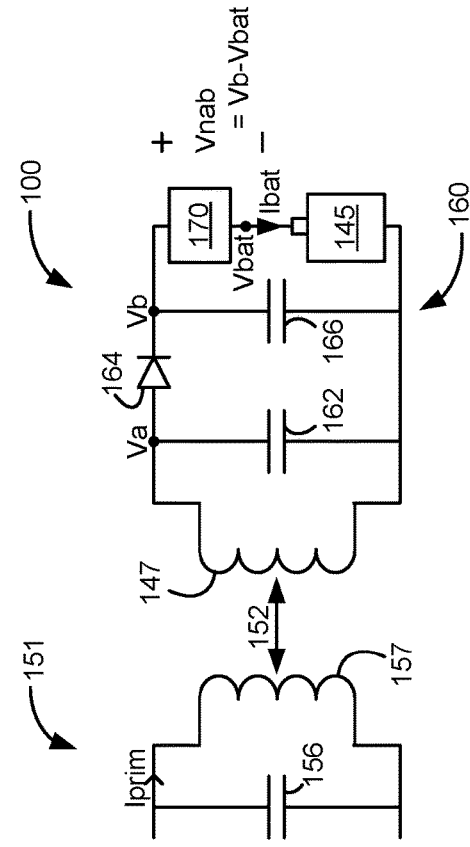
Figure 4:
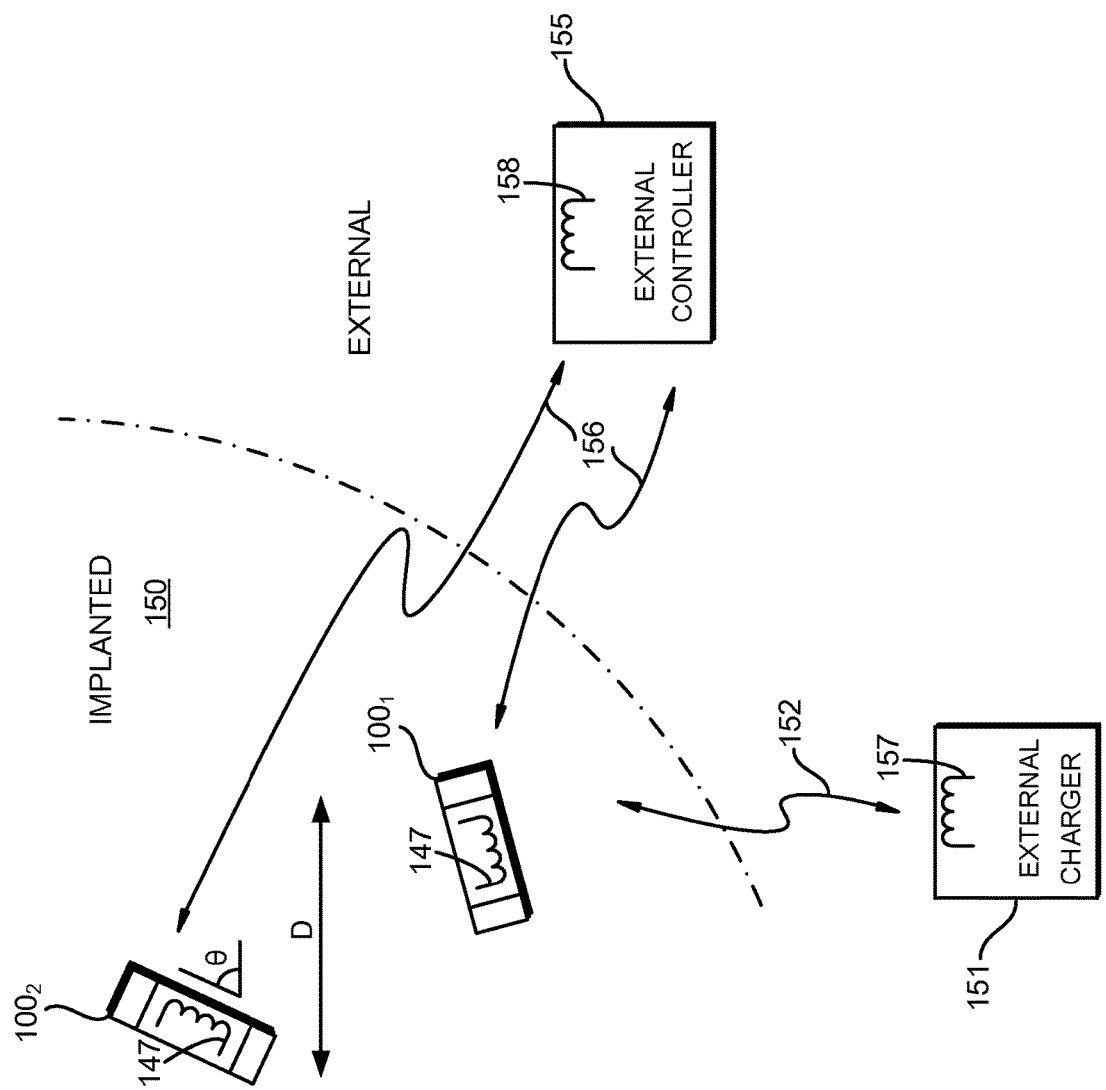
FIG. 4 illustrates multiple implants in communication with an external charger, in accordance with the prior art.
Figure 5B:
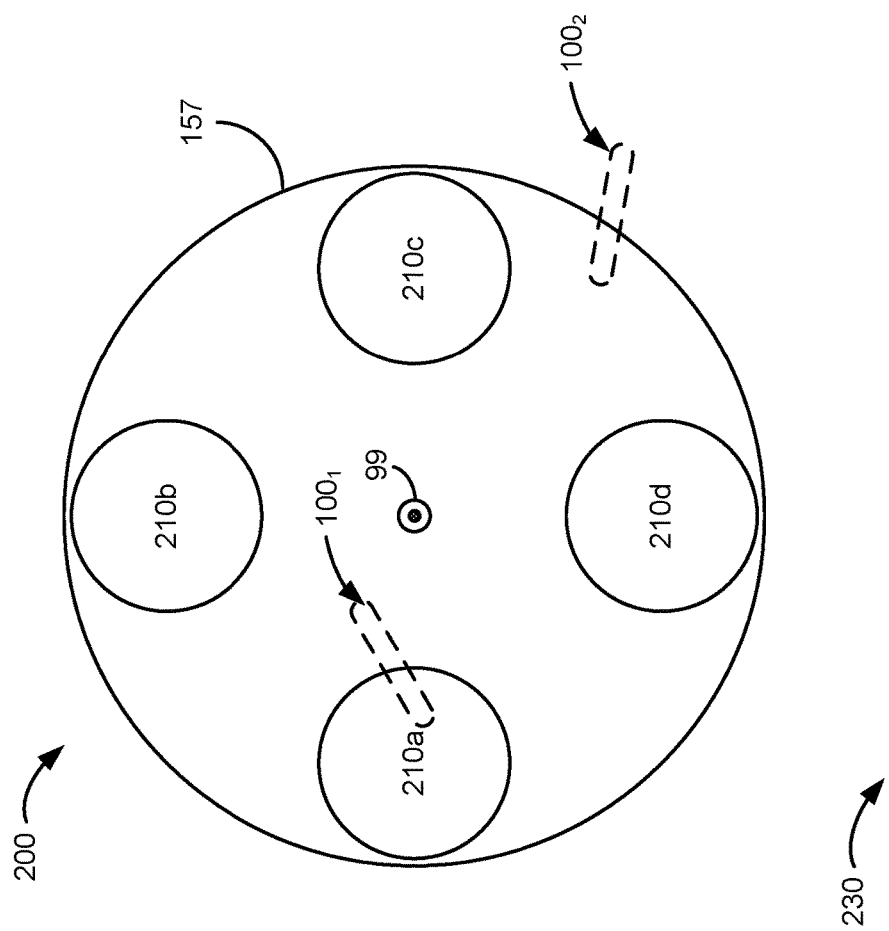

FIG. 5B quantifies such coupling data 230 between each of the microstimulators $100_1$ and $100_2$ and each of the field customization coils $210a\text{-}d$. Many different parameters could comprise the coupling data between each microstimulator and each coil $210a\text{-}d$, but in one embodiment, a parameter called Vnab is used. Using Vnab as a parameter indicative of coupling between an external charging coil and a coil in an implant is discussed at length in U.S. patent application Ser. No. 12/624,162 ("the '162 application"), filed Nov. 23, 2009, which is incorporated herein by reference in its entirety, and is therefore only briefly explained here. Referring again to FIG. 3B, Vnab comprises a voltage in the power circuitry 160 within the implant 100, and in particular comprises a voltage drop across the charging circuitry 170 when the power circuitry 160 is receiving a magnetic charging field. Vnab is computed as the difference between the DC rectified voltage, Vb, and the battery voltage, Vbat, i.e., Vnab=Vb−Vbat. As explained in the '162 application, Vnab scales with the power received from the external charger. Because the degree of coupling will affect the receipt of such power, Vnab is indicative of the coupling. As such, Vnab can comprise (or can be used to derive) a coupling coefficient, and is used directly as coupling data 230 in FIG. 5B. Notice that the example coupling data 230 shown in FIG. 5B is consistent with the physical positioning of the microstimulators $100_1$ and $100_2$ relative to the various field positioning coils $210a\text{-}d$: Vnab is high for microstimulator $100_1$ relative to coil $210a$ while Vnab is low for microstimulator $100_2$ relative to that coil, etc. Notice that Vnab takes into account all factors affecting coupling, including distance, offset, and angle between the microstimulators and the external charger 200.

Figure 5C:
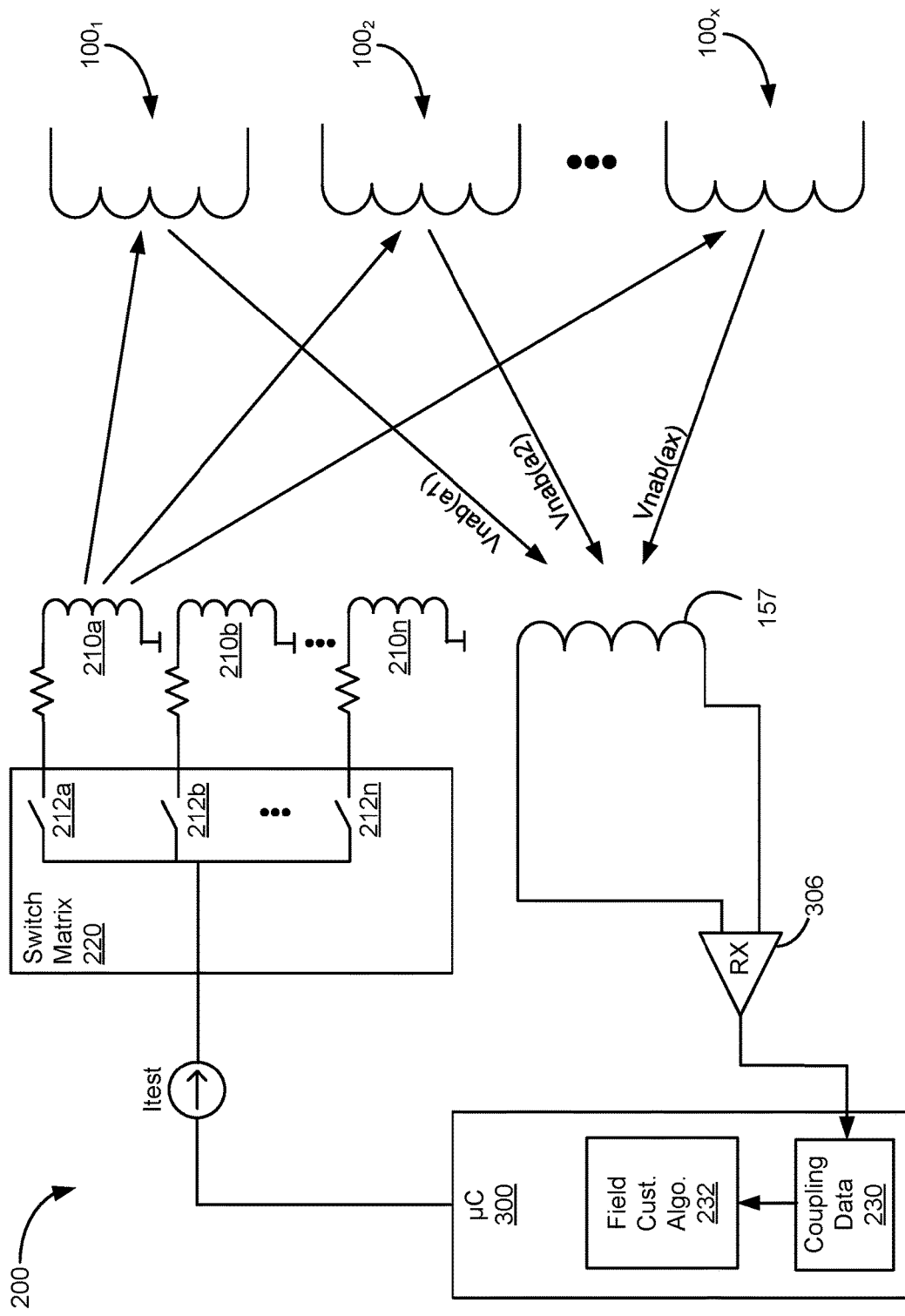

Because Vnab comprises a parameter originating at the microstimulators, may be telemetered to the external charger 200 for assessment, and FIG. 5C shows further details of how this is accomplished during the testing phase. Specifically shown is a test current, Itest. Although the routine details of the current source circuitry used to produce Itest are not illustrated for simplicity, the issuance of such current is ultimately controlled by the microcontroller 300 in the external charger 200. The test current is applied in sequence to each of the field customization coils 210, with a generic number, n, of such coils shown in FIG. 5C. Such sequential application of the test current Itest can occur via switches 212 in a switch matrix 220, which switches 212 are again ultimately controlled by the microcontroller 300.

When switch 212a is closed, field customization coil $210a$ is energized, and emits a test magnetic field that is received at each of the microstimulators 100. A generic number, x, of such microstimulators $100_1\text{-}100_x$ are shown in FIG. 5C. In response to receipt of the test magnetic field from field customization coil $210a$, each of the microstimulators will report their Vnab coupling data back to the external charger 200 in the manner discussed in the above-referenced '162 application. As shown, each of the reported Vnab values is indexed according to both the field customization coil that produced the test magnetic field (a-n) and the microstimulator receiving such field (1-$x$). For example, Vnab(a1) represents the Vnab parameter for the first microstimulator $100_1$ produced in response to a test magnetic field from coil $210a$. Once the Vnab data relevant to field customization coil $210a$ is received at the external charger 200 (i.e., Vnab(a1), (a2) . . . (ax)), switch $210b$ can be closed to procure data relevant to the next field customization coil (i.e., Vnab(b1), (b2) . . . (bx), etc.).

Figure 1:
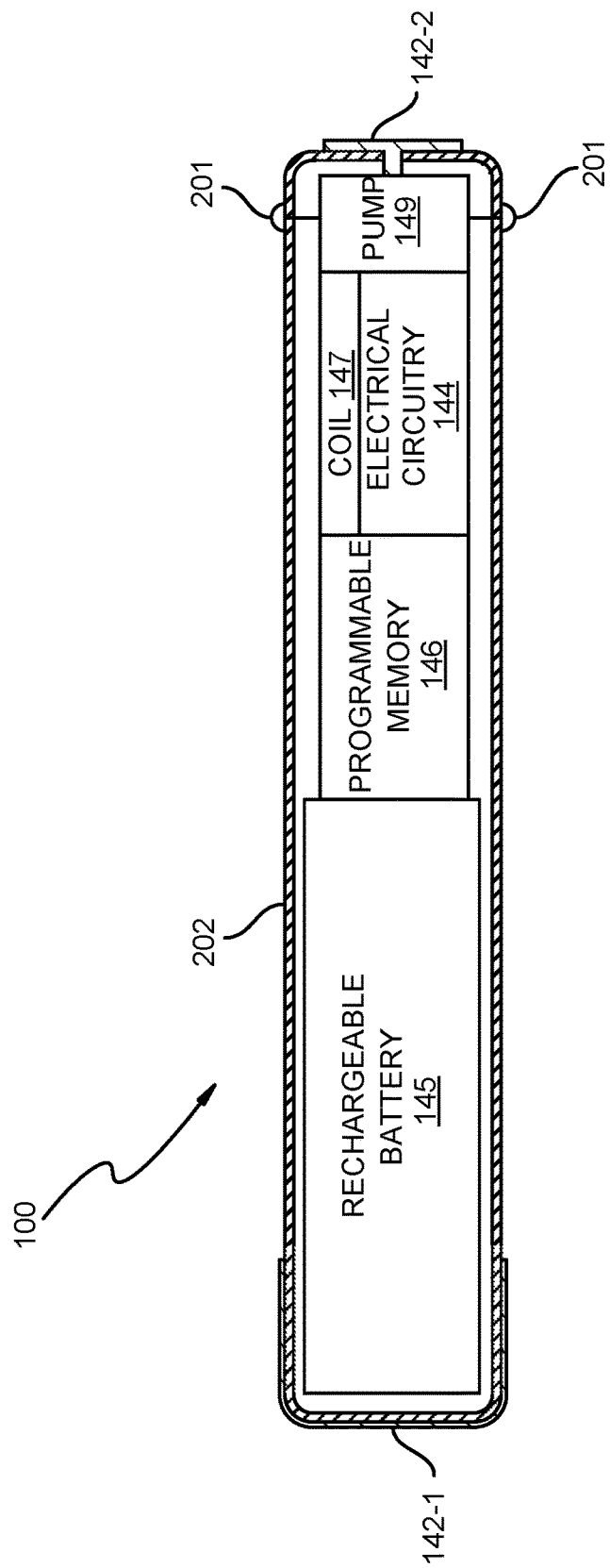
FIG. 1 illustrates a microstimulator implant, including a battery requiring recharging from an external charger, in accordance with the prior art.
Figure 2:
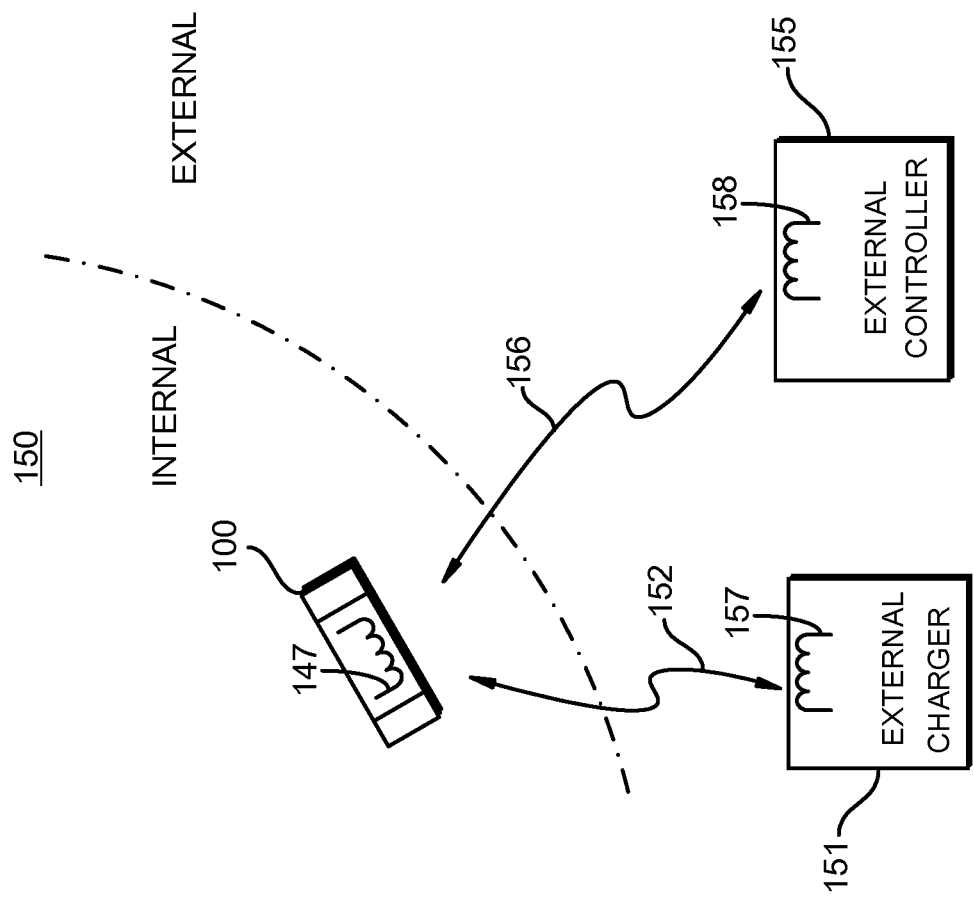
FIG. 2 illustrates the implant in communication with, inter alia, an external charger, in accordance with the prior art.

In the example shown in FIG. 5C, the Vnab coupling data is received by the primary coil 157. This can occur as described in the '162 application. For example, the microstimulators can transmit Vnab using telemetry circuitry (not shown) otherwise used to communicate with an external controller 155 (FIG. 2), although in this case it will be the external charger 200 that receives and demodulated this transmission. Such telemetry circuits typically operate pursuant to a Frequency Shift Keying (FSK) communication protocol, as is well known. Or, the microstimulator $100_1\text{-}100_x$ can use Load Shift Keying (LSK) in which the microstimulators vary the resistances of their coils 147 to produce detectable reflections in the test magnetic field. Still other telemetry protocols can be used to transmit the Vnab coupling data to the primary coil 157, and no particular telemetry protocol is important. Regardless of how the Vnab coupling data 230 is transmitted to the primary coil, it is demodulated at receiver 306 and stored in the external charger 200. Such storage may comprise memory on-board the microcontroller 300, but this is not strictly necessary; any memory associated with the microcontroller 300 can be used to store the coupling data 230.

Once the Vnab coupling data 230 is received, such data is analyzed by the microcontroller 300 to decide how logically to energize the field customization coils 210 during an actual charging session to tailor the magnetic charging field 201 (FIG. 5G) to best charge the various microcontrollers. Such decisions are made by a field customization algorithm 232 operating within (or in conjunction with) the microcontroller 300. The manner in which field customization algorithm 232 can work are varied and subject to designer preferences, but a logical goal of the algorithm 232 is to selectively energize the field customization coils 210 to tailor the magnetic charging field 201 to unify the energy each of the microstimulators is receiving. For example, consider the coupling data 230 in FIG. 5B: because the coupling between field customization coil $210a$ and microstimulator $100_1$ is relatively high, it may be desirable to decrease the strength of the magnetic charging field 201 at the location of coil $210a$. Alternatively, because the coupling is generally low between microstimulator $100_2$ and all of the coils, but is highest with respect to coil $210c$, it may be desirable to amplify the magnetic charging field at that coil $210c$, particularly if that coil $210c$ does not have a relatively high coupling to microstimulator $100_1$. Whether the magnetic charging field 201 is decreased at $210a$ or increased at $210c$, the effect will be that microstimulators $100_1$ and $100_2$ will receive closer to the same amounts of energy from the magnetic charging field and will therefore be charged more uniformly, and with less concerns over excessive heating or overly-slow charging by one of the microstimulators.

Figure 5D:
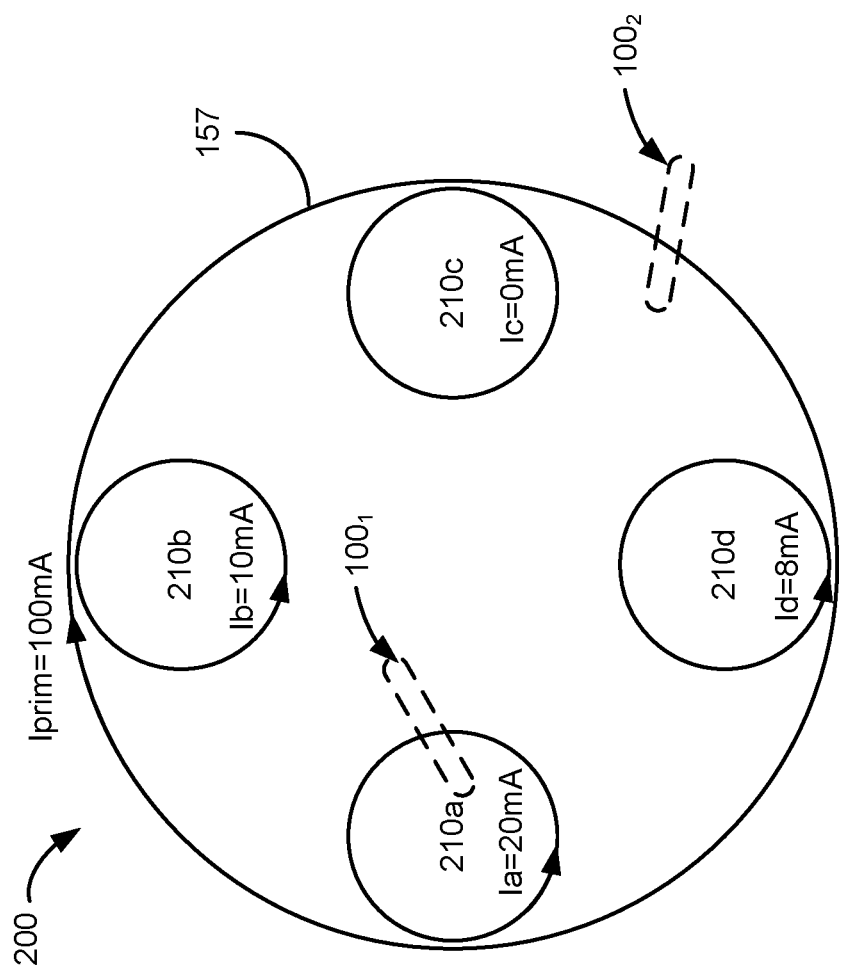

FIG. 5D shows one example of the practical output of the operation of the field customization algorithm 232, and shows how the primary coil 157 and the field customization coils $210a\text{-}d$ could be biased during a charging session. As shown, the primary coil 157 will be energized with a generally suitable baseline AC current, Iprim, which is shown as 100 mA in one example. An appropriate magnitude of this baseline current Iprim can be determined in other traditional manners. The field customization coils $210a\text{-}d$ are energized with customizing currents Ia-Id, which in the example shown in FIG. 5D flow in the opposite direction of the baseline current Iprim, and thus will tend to decrease the strength of the overall magnetic charging field 201 produced in those locations. For example, because of the high coupling between coil 210a and microstimulator $100_1$, the customization current Ia in that coil is relatively large (e.g., 20 mA) to deemphasize the magnetic charging field at that location. Customization currents Ib and Id in coils 210b and 210d are smaller, and thus will not so significantly decrease the magnetic charging field there. In coil 210c, which has the lowest coupling to both of the microstimulators $100_1$ and $100_2$, there is no customization current (i.e., Ic=0 mA) therefore keeping the magnetic field near peak strength proximate to that coil. Note that the various customization currents Ia-Id and the baseline current Iprim are preferably in phase to produce predictable and desired shaping of the magnetic charging field 201.

Figure 5E:
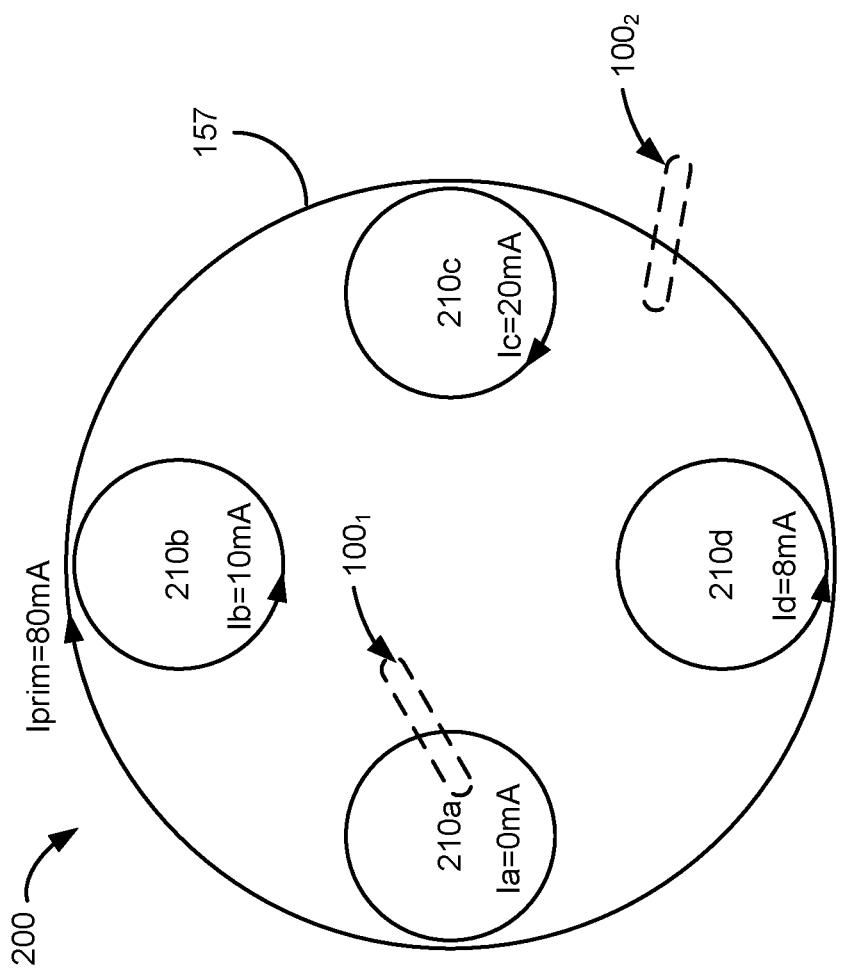

FIG. 5E shows other exemplary customization currents Ia-Id that could be used, although, in this instance the customization currents flow in the same direction as the baseline current, Iprim, which bolsters the magnetic field produced by the primary coil 157. In this instance, the customization current at coil 210c (Ic) is the highest, while no customization current is present at coil 210a (i.e., Ia=0 mA), which generally works the same effect as the deemphasizing customization currents of FIG. 5D.

Figure 5F:
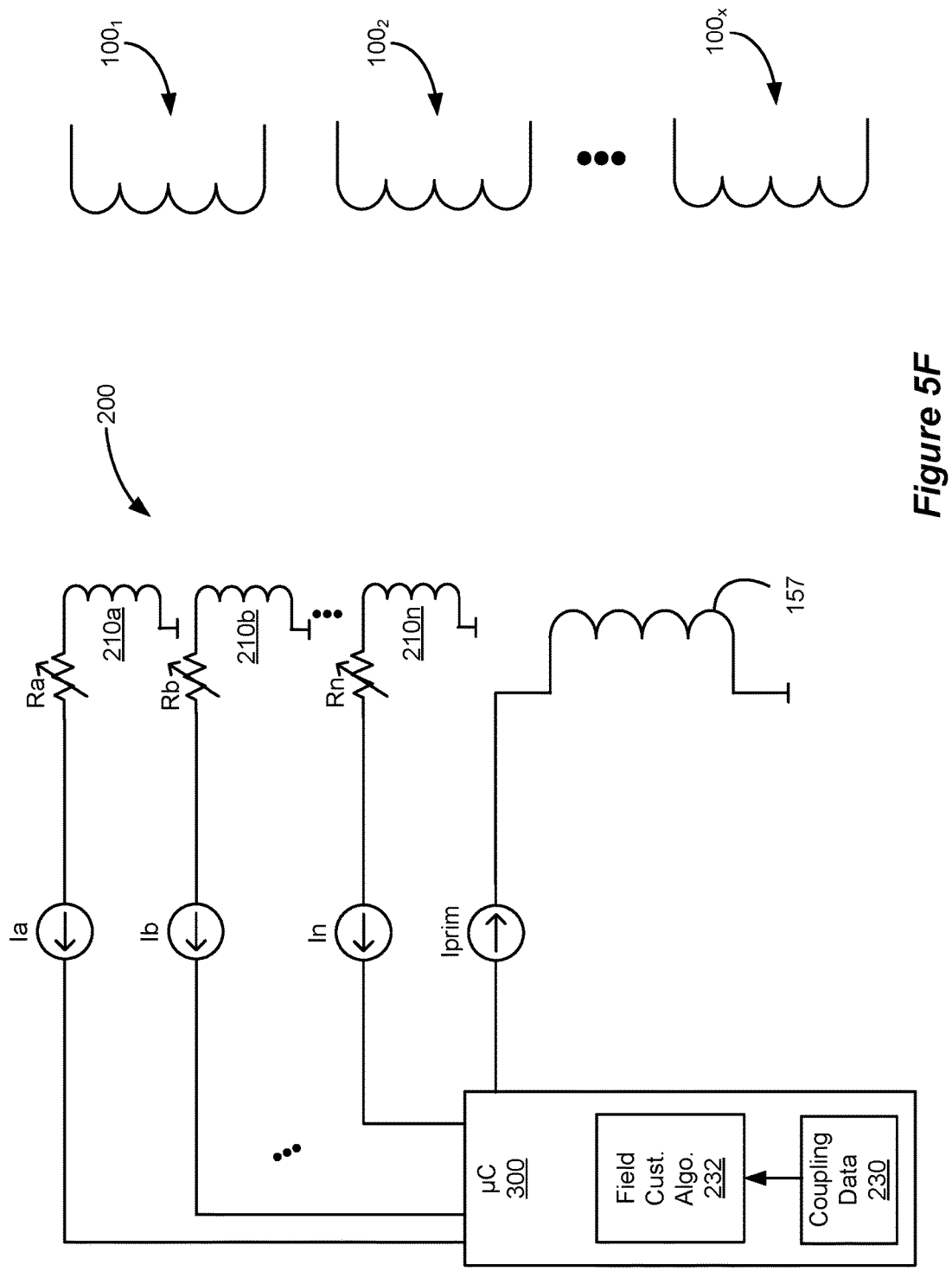

FIG. 5F shows circuitry for setting the magnitudes of the customization currents during an actual charging session. The depicted circuitry assumes that deemphasizing customization currents are used, as in FIG. 5D, because they flow in the opposite direction of the baseline current, Iprim. The microcontroller 300, in response to the algorithm 232, can set the current source circuitry feeding each of the field customization coils 210 to produce a logical customization current for each. In some embodiments, adjustable resistances Ra-Rn can be of assistance in tuning the customization currents to the right levels, particularly if the field customization coils 210a-d are energized by a constant voltage or current.

Figure 5G:
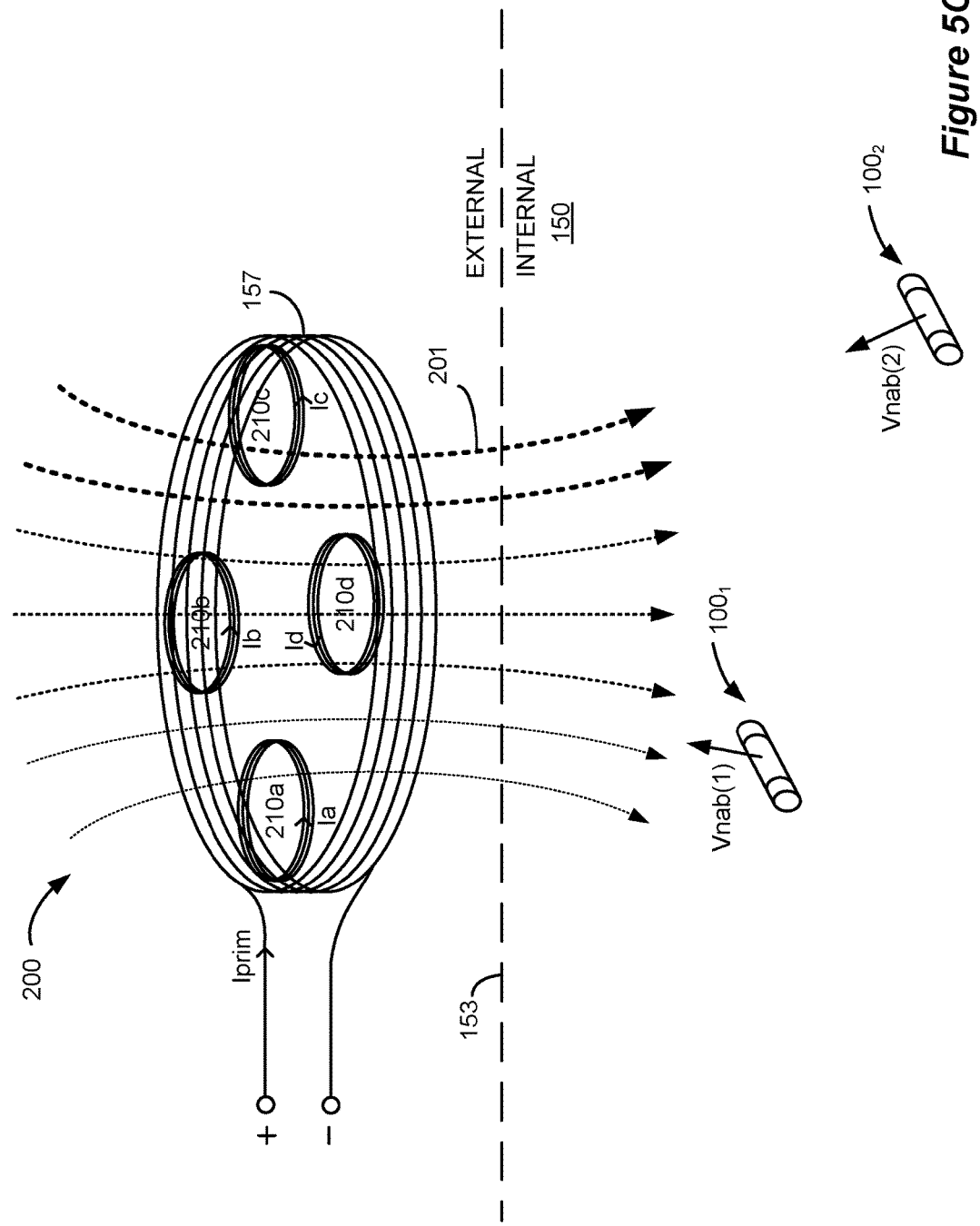

FIG. 5G shows the effect of the field customization coils on the magnetic charging field 201 during an actual charging session. (FIG. 5G depicts the use of deemphasizing customization currents Ia-Id, as shown in FIG. 5D, although once again emphasizing current as shown in FIG. 5E could also be used). As represented by different line thicknesses, the magnetic charging field 161 is not radially symmetric due to the different customization currents Ia-Id. The magnetic charging field 201 has been deemphasized at the left edge of the external charger 200 near microstimulator $100_1$ to compensate for that device's relatively high coupling, yet the field is retained at near full strength proximate to microstimulator $100_2$ having relatively low coupling.

After setting the customization currents, Vnab parameters can continue to be reported from the microstimulators $100_1$ and $100_2$ during the charging session (i.e., Vnab(1), Vnab (2), . . . Vnab(n)) as shown in FIG. 5G. (Note that indexing to a particular field customization coil 210a-d is unnecessary when reporting Vnab values during the charging sessions, since all coils 210a-d and 157 act in unison). If the customization currents set during the testing phase were well chosen, then one would expect the Vnab parameters reported from each of the microstimulator to be the same, or at least closer, indicating that each microstimulator is receiving approximately the same amounts of energy from the magnetic charging field 201, and thus will charge at approximately the same rates. If not, then it may be desirable to adjust the customization currents during the charging session to bring the Vnab data into line. For example, if it is seen that the Vnab value reported from microstimulator $100_1$ during the charging session is high relative to the Vnab values reported from microstimulator $100_2$, then perhaps customization current Ia can be increased (FIG. 5D) or decreased (FIG. 5E) to even further decrease the magnetic charging field 201 proximate to microstimulator $100_1$. That magnetic charging field customization can occur "on the fly" during a charging session is significant because it also allows for adjustments arising from movement of the external charger 200 relative to the microstimulators. Such movement will change the relative coupling between the microstimulators and each of the field customization coils 210a-d, and hence the customization currents Ia-Id would benefit from retuning should such movement occur.

Further to this observation, while it is convenient to have a testing phase to set the customization currents Ia-Id, this is not strictly necessary. A testing phase such as described above with respect to FIG. 5C allows the external charger 200 to have some idea of the relative positioning of the microstimulators $100_1$ and $100_2$, thus allowing the customization currents Ia-Id to be set to reasonable initial values. However, such testing can be dispensed with, and instead the field customization algorithm 232 can attempt to adjust the customization currents Ia-Id using a random or iterative search for the optimal changing conditions, i.e., by randomly or iteratively modifying the customization currents to produce the best uniformity in the reported Vnab values during charging.

FIGS. 6A to 6F illustrate a second embodiment of an improved external charger 200'. External charger 200' is similar to charger 200 discussed previously, except that it lacks a primary coil 157, as can be seen in FIGS. 5A-5B. Instead, only field customization coils 210a-210d are used, which can essentially be the same as those discussed with respect to external charger 200. Because external charger 200' lacks a primary coil 157, both the testing phase and the charging session are modified, and such modifications are discussed.

Figure 6B:
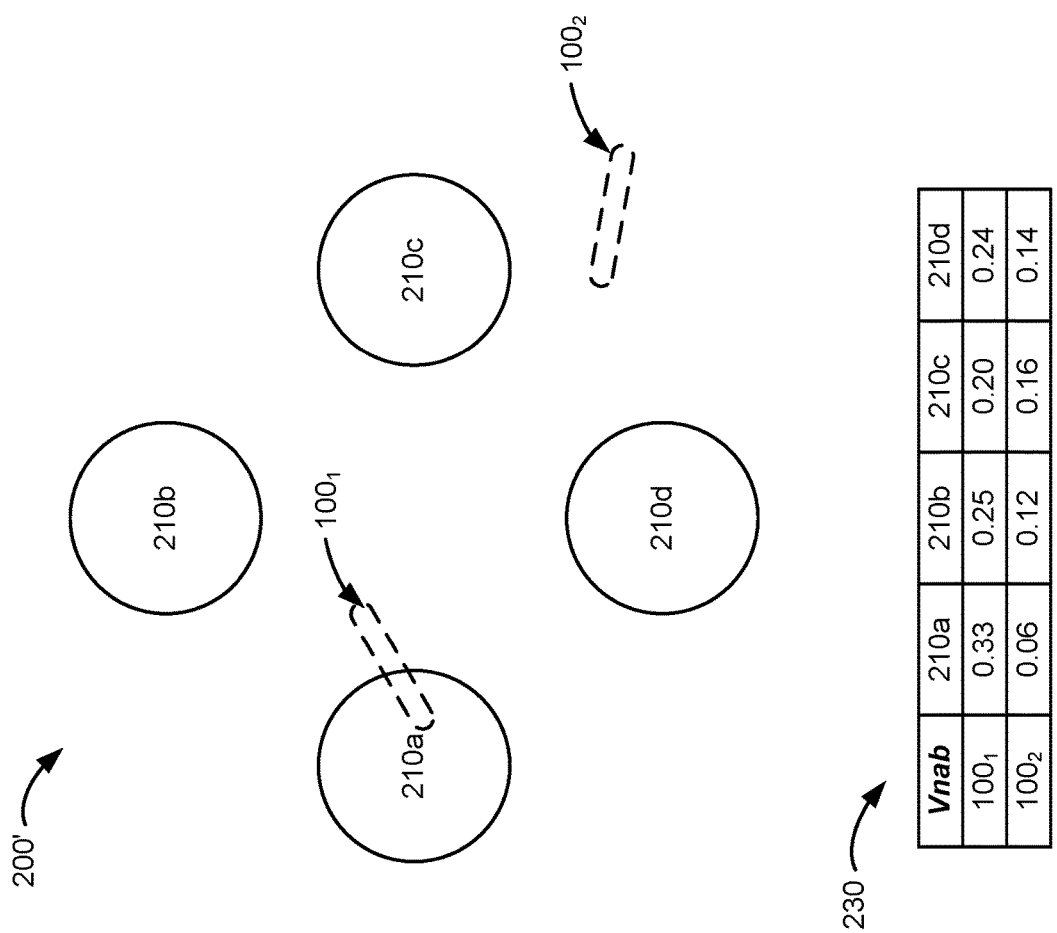
Figure 6C:
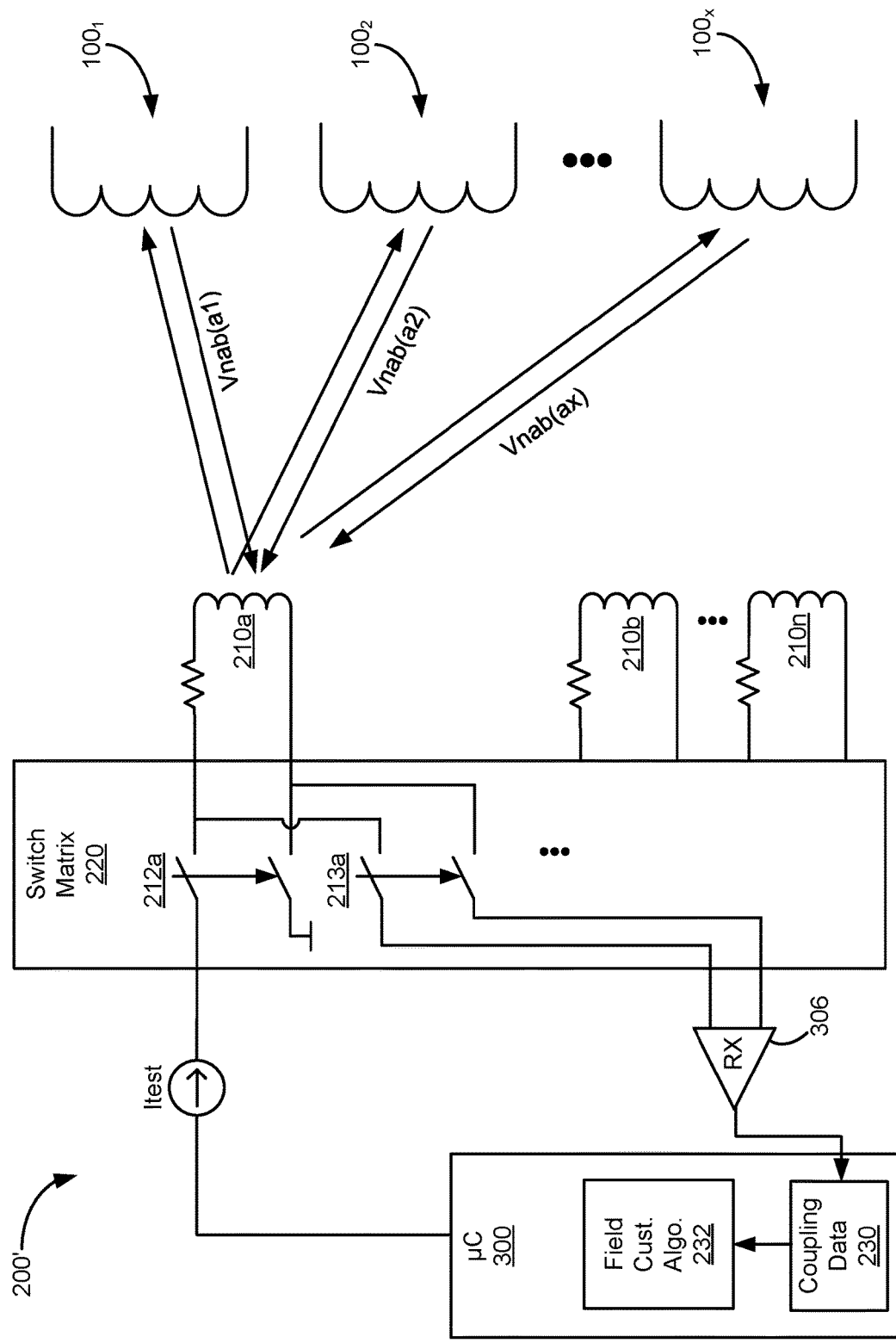

FIG. 6C illustrates circuitry involved in the testing phase in which the various couplings between the microstimulators $100_1$ and $100_2$ and the field customization coils 210a-d are deduced. As before, switch matrix 220 control access to the various field customization coils, and each coil is associated with two groups of switches 212 and 213. Switches 212 couple their associated coil to the test current Itest, while switches 213 simultaneously couple that coil to the receiver 306. This allows each coil 210, in succession, to send a test magnetic field to each of the microstimulators 100. As before, each of the microstimulators 100 will send a coupling parameter (e.g., Vnab) to the external charger 200'. However, because there is no primary coil 157 in external charger 200' to receive such transmission from the microstimulators 100, the transmissions are instead received by the transmitting field customization coil 210, which coil is then coupled to receiver 306 via switches 213. An LSK data communication protocol can be used to transmit the Vnab coupling data 230, but this is not strictly required, and switches 212 and 213 do not need to be simultaneously closed for each coil 210.

Figure 6D:
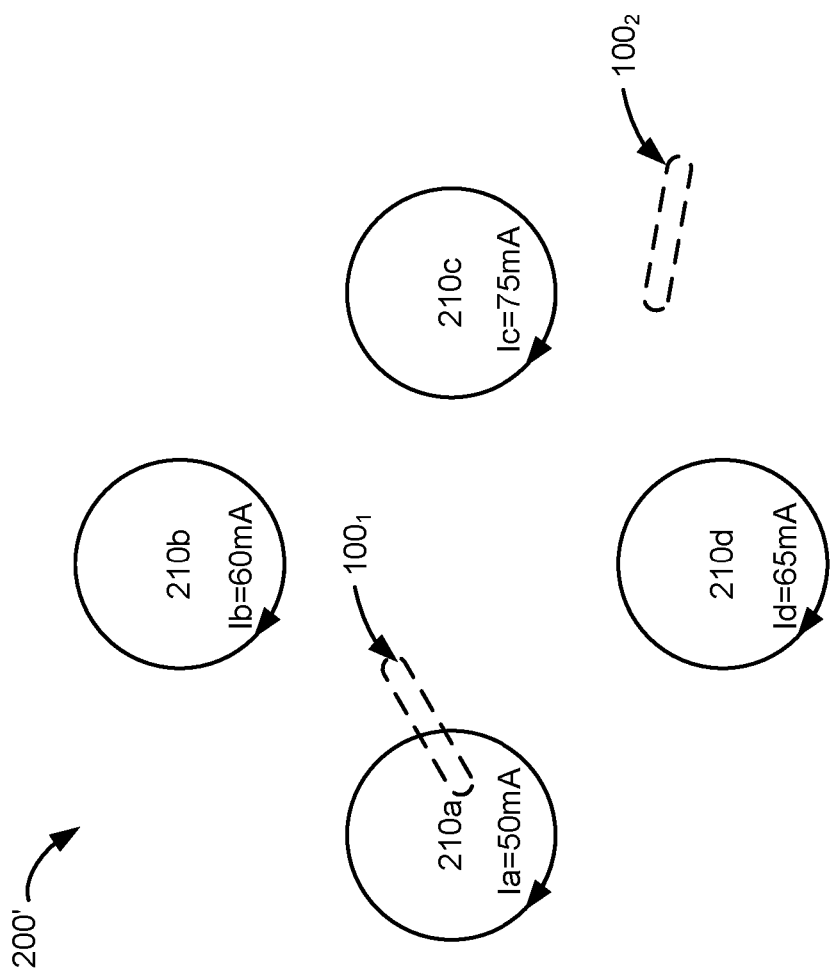
Figure 6E:
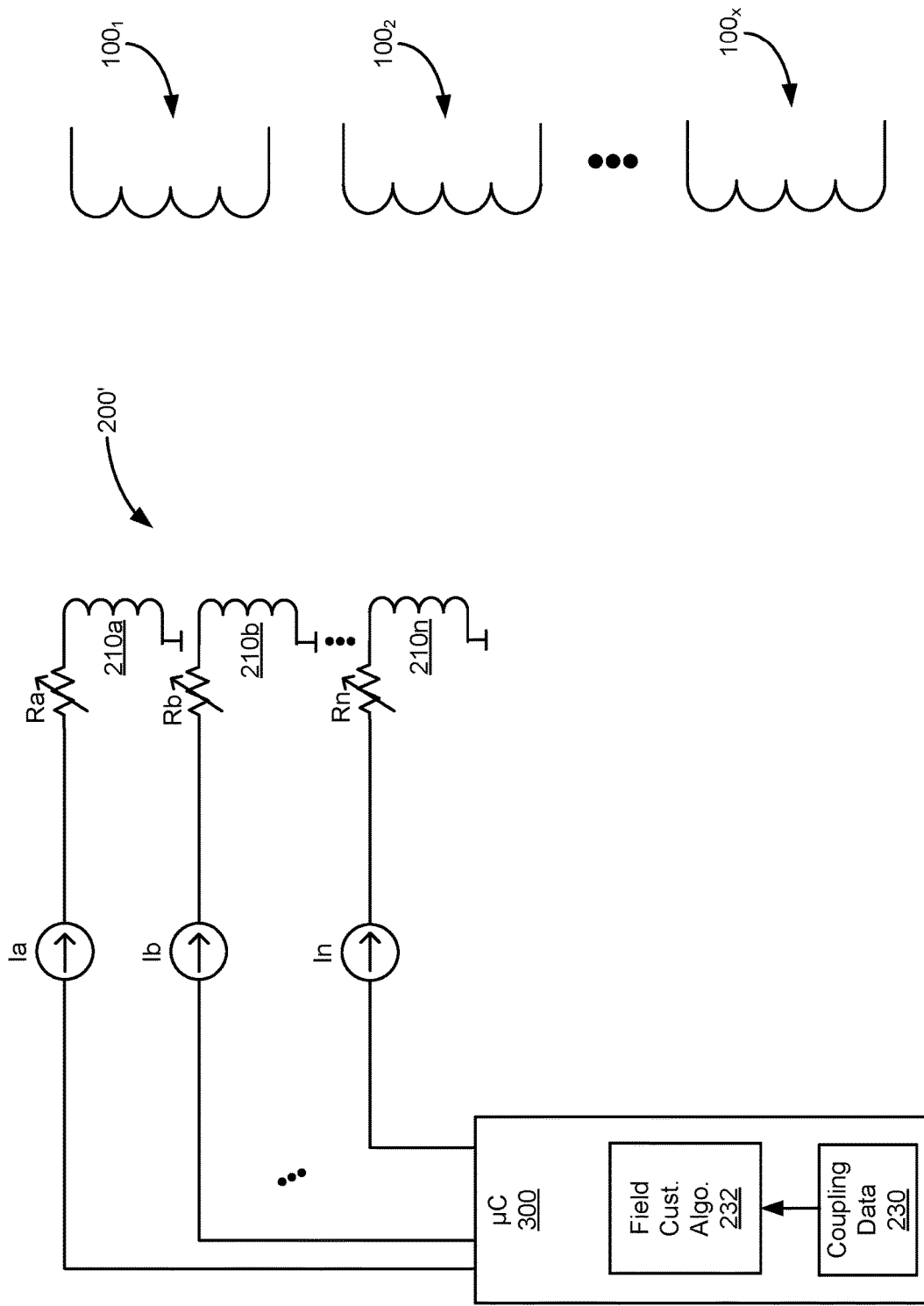
Figure 6F:
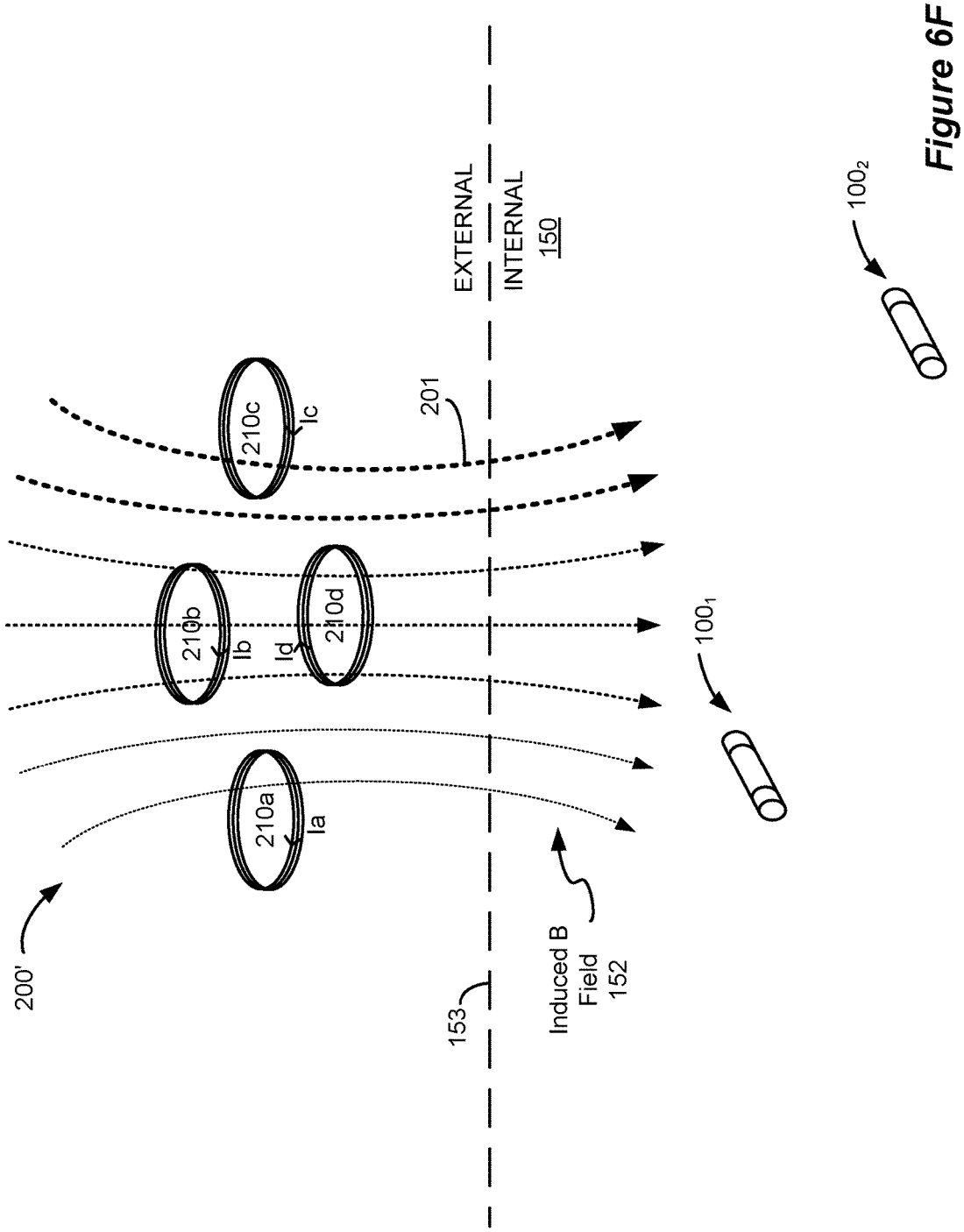

Regardless of the particular protocol used, the reported Vnab coupling data 230 (FIG. 6B) will be similar to that received for external charger 200, and will likewise be stored and processed by the field customization algorithm 232, which will in turn generate appropriate customization currents Ia-Id for each of the field customization coils 210$a$-$d$ to use during an actual charging session. The field customization algorithm 232 in this case must account for the lack of the primary coil 157, and must recognize that the field customization coils 210$a$-$d$ must provide all of the necessary energy for the magnetic charging field 201, instead of merely perturbing such energy from the primary coil 157 as occurred earlier. The field customization algorithm therefore may need to prescribe higher customization currents Ia-Id for the field customization coils 210$a$-$d$. For example, and as shown in FIG. 6D, each of the coils 210$a$ is biased with relatively high currents (ranging from 50-75 mA), which currents will not only customize the produced magnetic charging field 201, but will provide such field with sufficient energy for charging the microstimulators $100_1$ and $100_2$. Of course, the actual magnitudes of the customization currents will depend on many factors, such as the number of turns in each of the field customization coils 210$a$-$d$ and the currents shown in FIG. 6D are merely examples to illustrate the technique. Note in FIG. 6D that the customization currents Ia-Id all follow the same direction (e.g., clockwise), and so act in sum to produce the desired magnetic charging field 201. However, because customization current Ia on the left edge is smaller than customization current Ic on the right edge, the produced magnetic charging field will be decreased in the vicinity of microstimulator $100_1$ (which has relatively high coupling) and increased in the vicinity of microstimulator $100_2$ (which has relatively low coupling) as desired, and as is shown in FIG. 6F. Although not mentioned, it will be appreciated that the modifications discussed above with respect to external charger 200 will also apply to external charger 200', which modifications are not again discussed for simplicity.

FIGS. 7A to 7E illustrate another embodiment of an improved external charger 200". This embodiment 200", like the first 200, includes a primary coil 157 in additional to the field customization coils 210$a$-$d$. However, unique to this embodiment is the use of switches 250$a$-$d$ to selectively couple any of the field customization coils 210$a$-$d$ to the primary coil 157 during an actual charging session. Coupling the field customization coils to the primary coil can also be use to generate a radially asymmetric magnetic charging field 201 particularly useful in simultaneously charging a plurality of microstimulators.

Figure 7A:
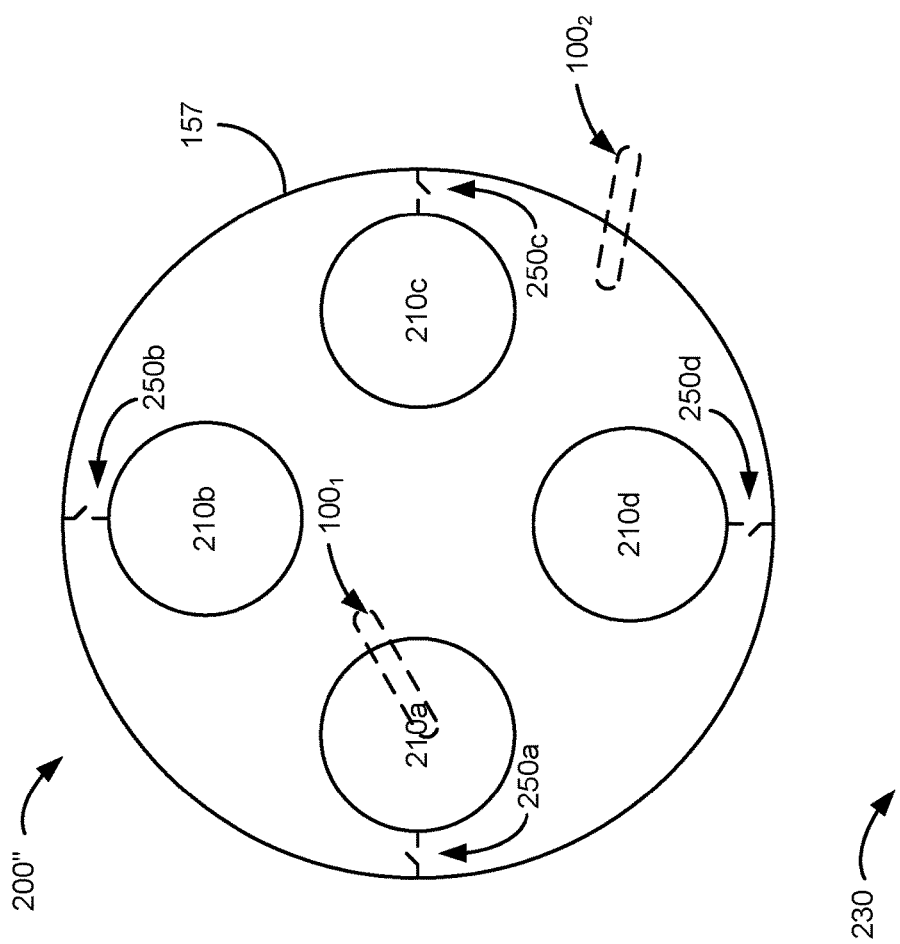
FIGS. 7A-7E illustrate the structure and operation of a third embodiment of an improved external charger particularly useful in charging a plurality of implantable medical devices, in which the charger comprises a plurality of field customization coils as well as a primary coil, in which the field customization coils are selectively coupleable to the primary coil.
Figure 7B:
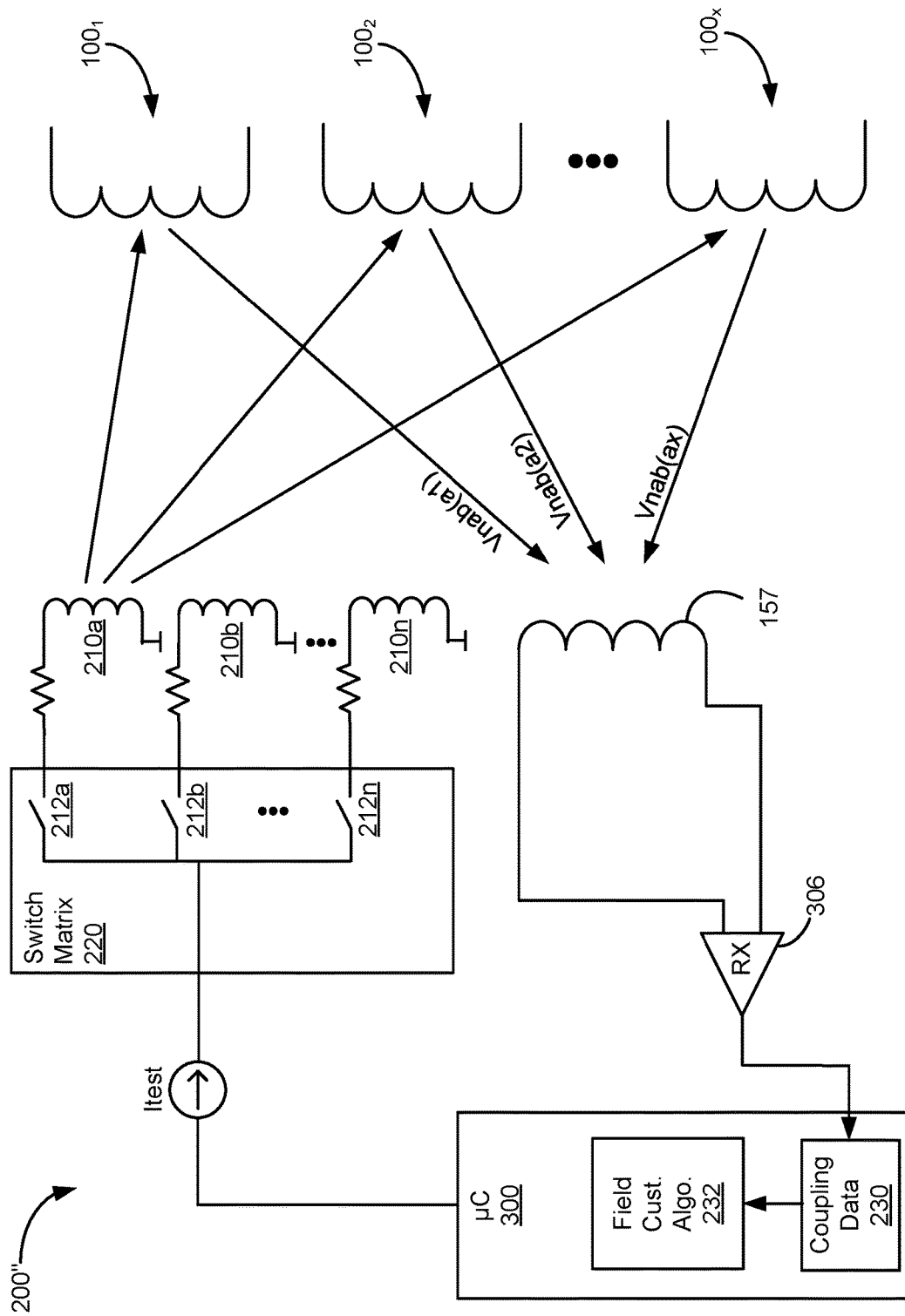

FIGS. 7A and 7B show aspects of external charger 200" that are essentially similar to external charger 200, and illustrate the testing phase for determining the coupling data 230 between the field customization coils 210$a$-$d$ and the microstimulators $100_1$ and $100_2$. As before, each of the field customization coils 210$a$-210$n$ is sequentially activated to produce a magnetic test field. In response to that field, each microstimulator reports its Vnab coupling data, which can be received at the primary coil 157/receiver 300 and ultimately stored for use by the field customization algorithm 232.

Figure 7C:
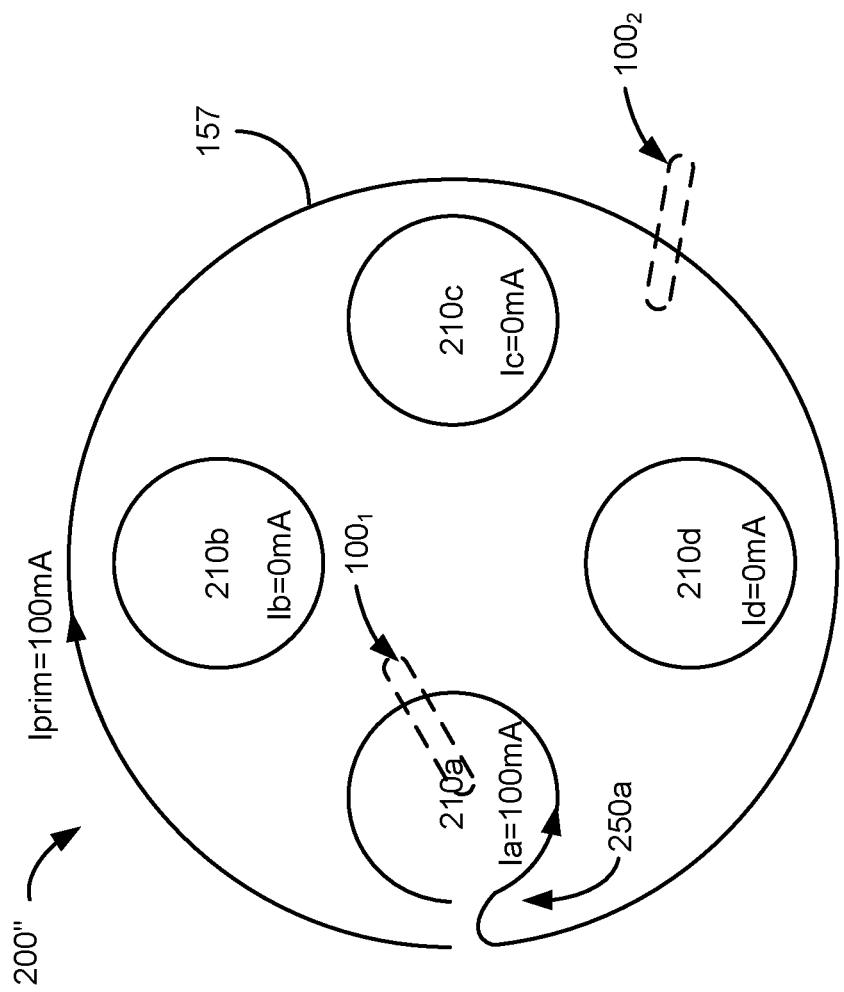
Figure 7D:
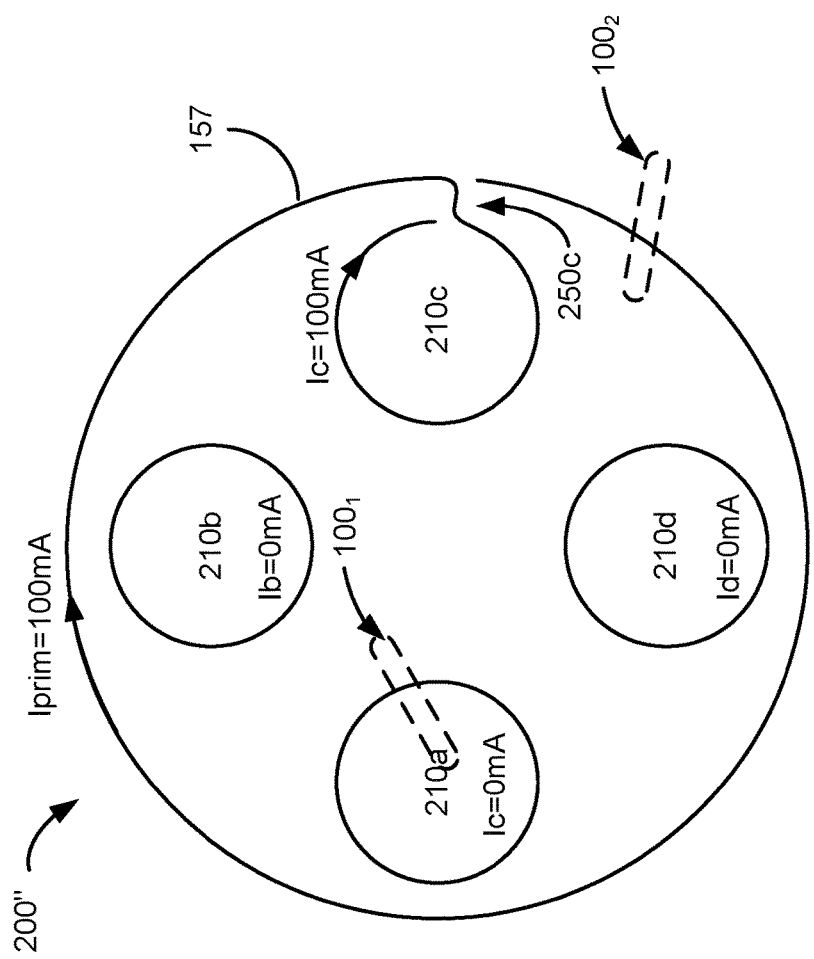

The field customization algorithm 232 as before will assess the reported coupling data 230 to determine which areas of the magnetic charging field 201 will need emphasis or deemphasis. For example, if field customization algorithm 232 determines that the magnetic charging field 201 needs deemphasis proximate to field customization coil 210$a$ because of high coupling to microstimulator $100_1$, then switch 250$a$ can be closed during charging to couple coil 210$a$ to the primary coil 157, as illustrated in FIG. 7C. As shown, switch 250$a$ couples the primary coil 157 and field customization coil 210$a$ in series, so that both coils receive the excitation current, Iprim. However, because the customization current Ia in coil 210$a$ flows opposite the current in coil 157 (counterclockwise v. clockwise), the overall effect will be to deemphasize the magnetic charging field 201 at the location of coil 210$a$ as desired. Reversing the current flow in the in the field customization coils 210$a$-$d$ to deemphasize field 201 can be effected by either winding these coils 210$a$-$d$ with appropriate orientations, or placing the switches at appropriate ends of the coils 210$a$-$d$. Alternatively, the current in the customization coil can also be made to flow in the same direction as the current in the primary coil 157, thus emphasizing the magnetic charging field 201 at the location of that coil. For example, if it is desired to emphasize the field 201 at coil 210$c$ because of low coupling to microstimulator $100_2$, switch 250$c$ could be close as shown in FIG. 7D to cause customization current Ic to flow in the same direction as Iprim.

Figure 7E:
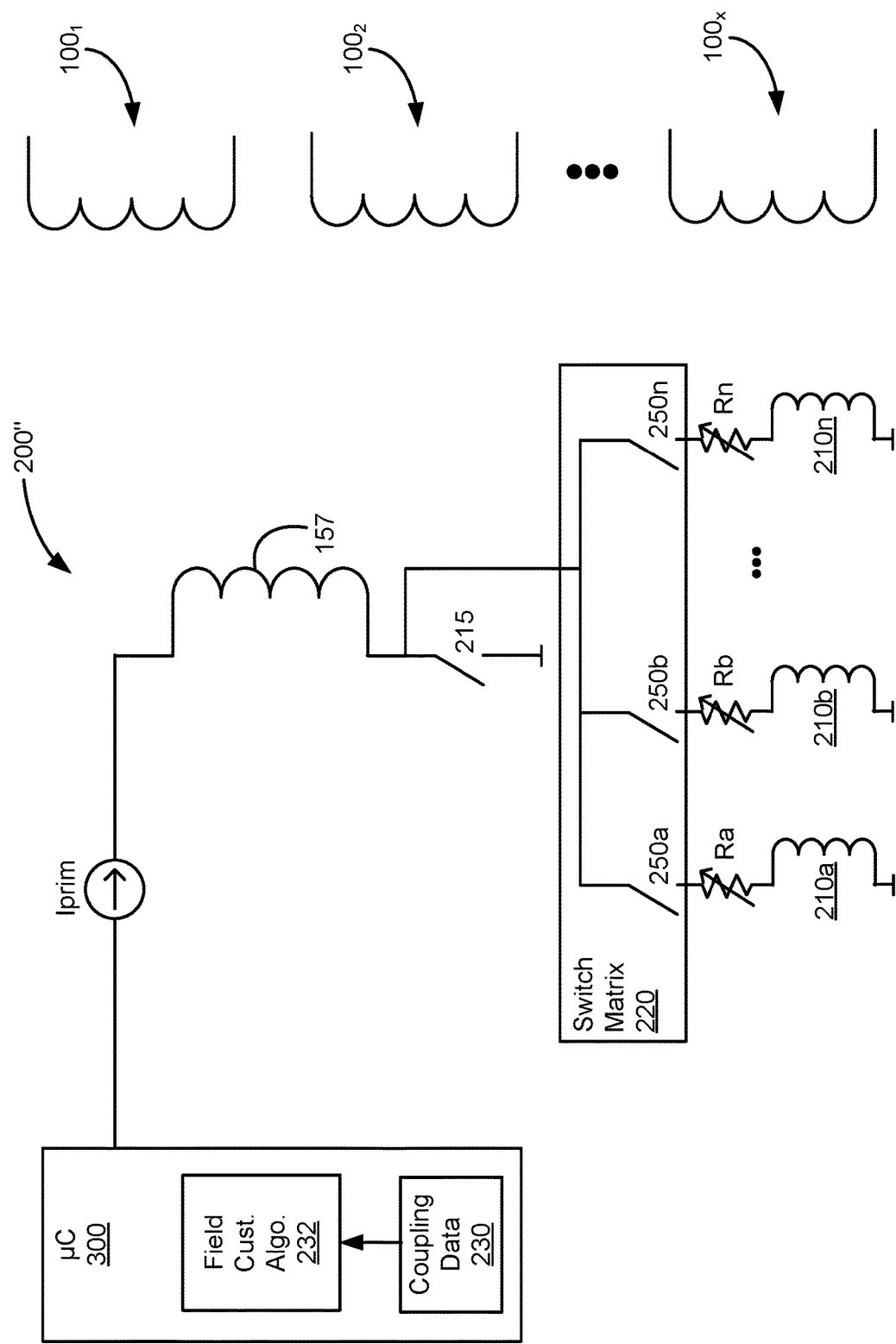

FIG. 7E shows circuitry for routing the excitation current Iprim through the field customization coils 210$a$-$n$ during an actual charging session. Shown in switch matrix 220 are switches 250$a$-$n$ which as already noted are used to connect the primary coil 157 and any of the field customization coils 210$a$-$n$ in series. Also shown in switch 215, which is used to ground one end of the primary coil 157 should none of the field customization coils 210$a$-$n$ be connected in series, i.e., if none of switches 250$a$-$n$ are closed. As shown, the paralleled relationship of the field customization coils 210$a$-$n$ make it so that more than one of the field customization coils can be coupled to the primary coil 157, in which case the excitation current would be split between those coils 210$a$-$n$ in accordance with their resistances. Although not shown in FIG. 7E, field customization coils 210$a$-$n$ could also be connected in series.

The extent to which the field customization coils 210 in external charger 200" will emphasize or deemphasize the magnetic charging field depends on various factors, including the number of turns of coils 210, the resistance of the windings, their diameters, etc. Additional adjustable resistances Ra-Rn can assist in allowing the effect of each of the coils 210 to be tailored.

Although not illustrated, another basic form of customization for an improved external charger is to simply selectively open or close the field customization coils 210$a$-$d$. An open field customization coil will not allow current to flow and therefore will have minimal impact on the field generated by the primary coil. A closed field customization coil will capture energy from the primary coil 157 and, due to magnetic induction and Lenz's law, will generate a field that will weaken the magnetic field generated by the primary coil at the location of the closed field customization coil, without needing additional current sources. This passive customization can be adjusted by adjusting a series resistance in the closed field customization coil, as shown in earlier embodiments, with a larger resistance corresponding to a lesser reduction in the primary field. Simple switches can be used to open the field customization coils, or to close them, e.g., by shorting each of the ends of the coils to a common node such as ground. Again, this embodiment is not illustrated because its circuitry should be obvious in light of circuitry depicted in earlier embodiments.

Embodiments of the improved external charger to this point have involved transmitting coupling data to the external charger from the various microstimulators 100. But this is not strictly necessary, and FIGS. 8A-8D illustrate a fourth embodiment of an external charger 200'" in which coupling to the various microstimulators 100 is measured at the external charger 200'" without telemetry. Any of the previous configurations for the external charger could be used (with or without a primary coil 157; without or without series switches 250*a*-*d*), but the example external charger 200''' shown in FIGS. 8A-8D includes a primary coil 157 without series switches 250*a*-*d*, and so is similar to external charger 200 of FIGS. 5A-5G.

Figure 8B:
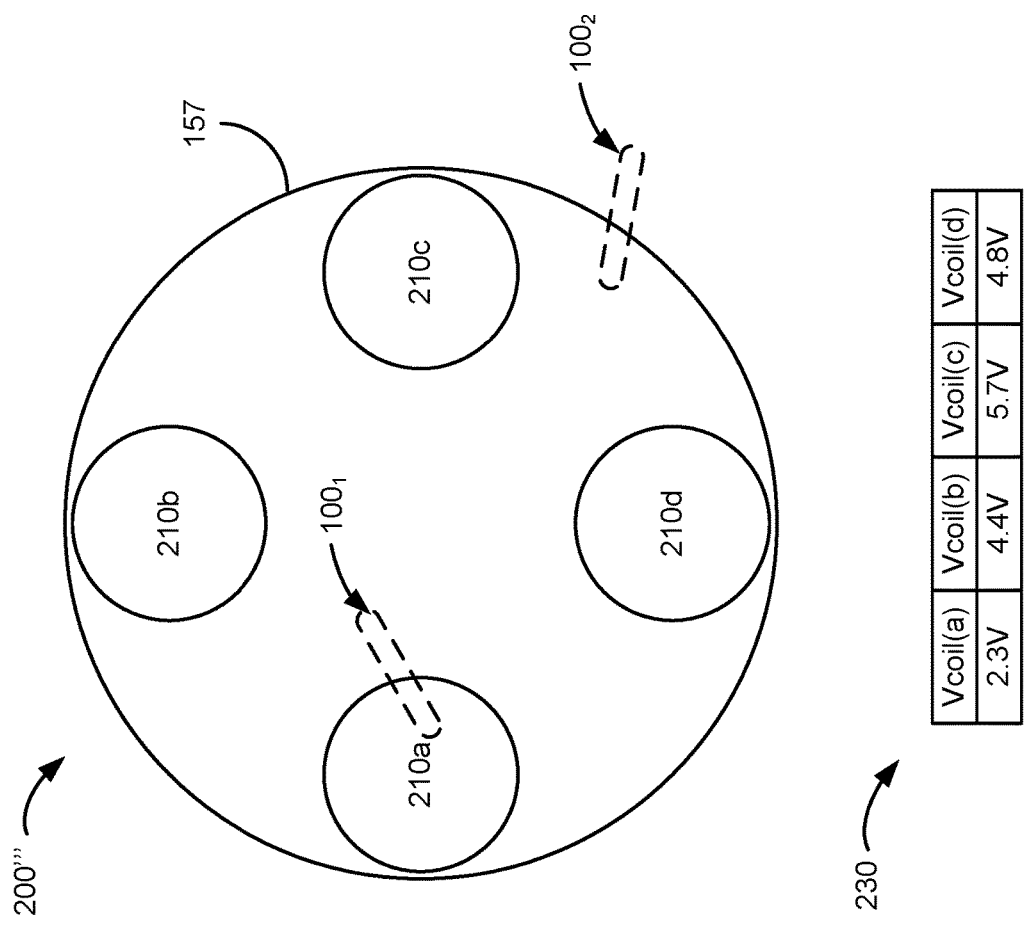
Figure 8C:
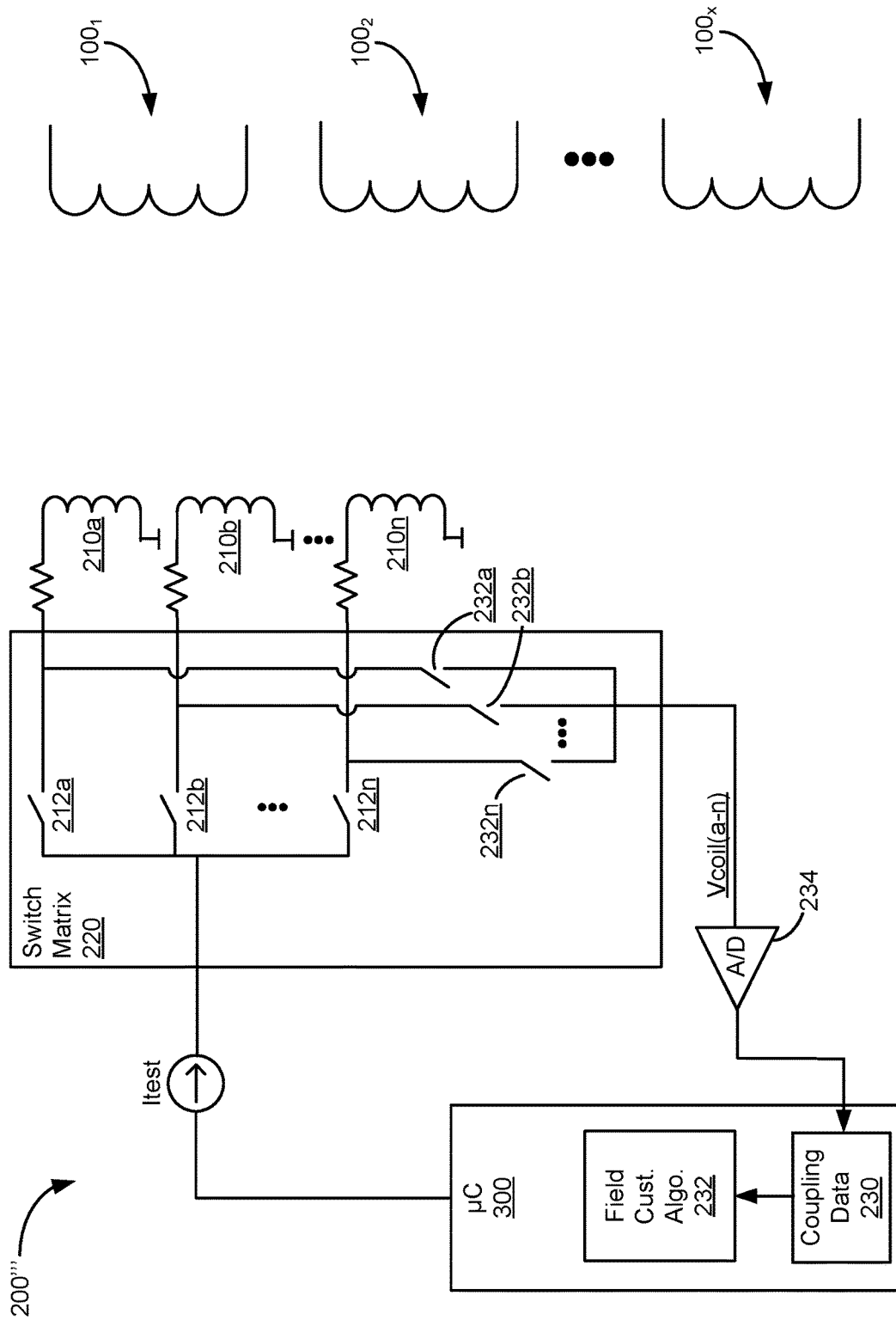

In external charger 200''', the coupling data does not comprise Vnab or any other parameter telemetered from the microstimulators $100_1$ or $100_2$. Instead, and as shown in FIG. 8B, coupling data comprises a voltage measured across each of the field customization coils 210*a*-*d*, i.e., Vcoil(a)-(d). FIG. 8C shows the circuitry used during a testing phase to measure each of these coil voltages. As shown, a switch matrix 220 is included which contain switches 212*a*-*n*, which as in earlier embodiments are use to sequentially route a test current, Itest, to each of the field customization coils 210*a*-*n*. Additionally included in the switch matrix 220 are switches 232*a*-*n*. These switches 232*a*-*n*, like switches 212*a*-*n*, are sequentially closed to present the voltage across each of the coils (Vcoil(a-n)) to an Analog-to-Digital (A/D) converter 234, which voltages are then stored as the coupling data 230.

Figure 8D:
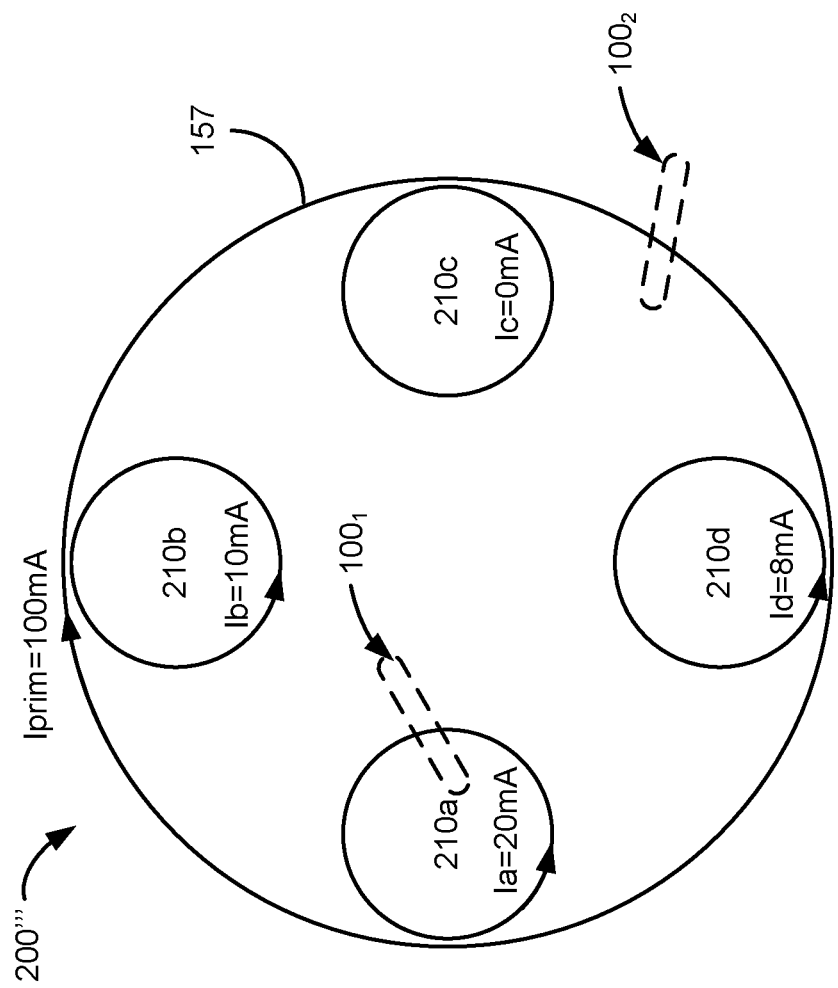

Like the telemetered Vnab parameters, Vcoil is also indicative of the coupling between each of the field customization coils 210*a*-*n* and the microstimulators $100_1$ and $100_2$. This is due to the mutual inductance between the coils 210*a*-*n* and the coils 147 in the microstimulators. As the coupling between the coils decreases—for example, if the coils become misaligned or are move farther apart—a high Vcoil voltage will be needed to support the specified test current, Itest, and as such this voltage is indicative of the coupling. The main difference in this instance is that Vcoil (a-n) is not specific to any particular microstimulator, e.g., $100_1$ or $100_2$. It simply quantifies coupling between one of the field customization coils 210*a*-*d* and any of the microstimulators $100_1$ or $100_2$. Although this coupling data 230 does not index a particular microcontroller 100, it still informs the external charger 200''' which of the field customization coils 210*a*-*n* have a high coupling (to some microstimulator regardless of its position) and thus needs deemphasizing. For example, note in FIG. 8B that Vcoil (a)—the voltage across field customization coil 210*a*—is relatively low. This will be interpreted by the field customization algorithm 232 as indicative of a high coupling between coil 210*a* and at least one of the microstimulators $100_1$ or $100_2$, and therefore at least one of the stimulators is at risk to charge with excessive heat without deemphasis at that coil. Likewise, because Vcoil(c) is relatively high, none of the microstimulators $100_1$ or $100_2$ has a high coupling to field customization coil 210*c*, and hence that coil's contribution to the magnetic charging field can be emphasized. In any event, the field customization algorithm 232 can use the measured Vcoil coupling data 230 to set the customization currents Ia-Id accordingly to tailor the magnetic charging field 201, as shown in FIG. 8D.

Figure 9A:
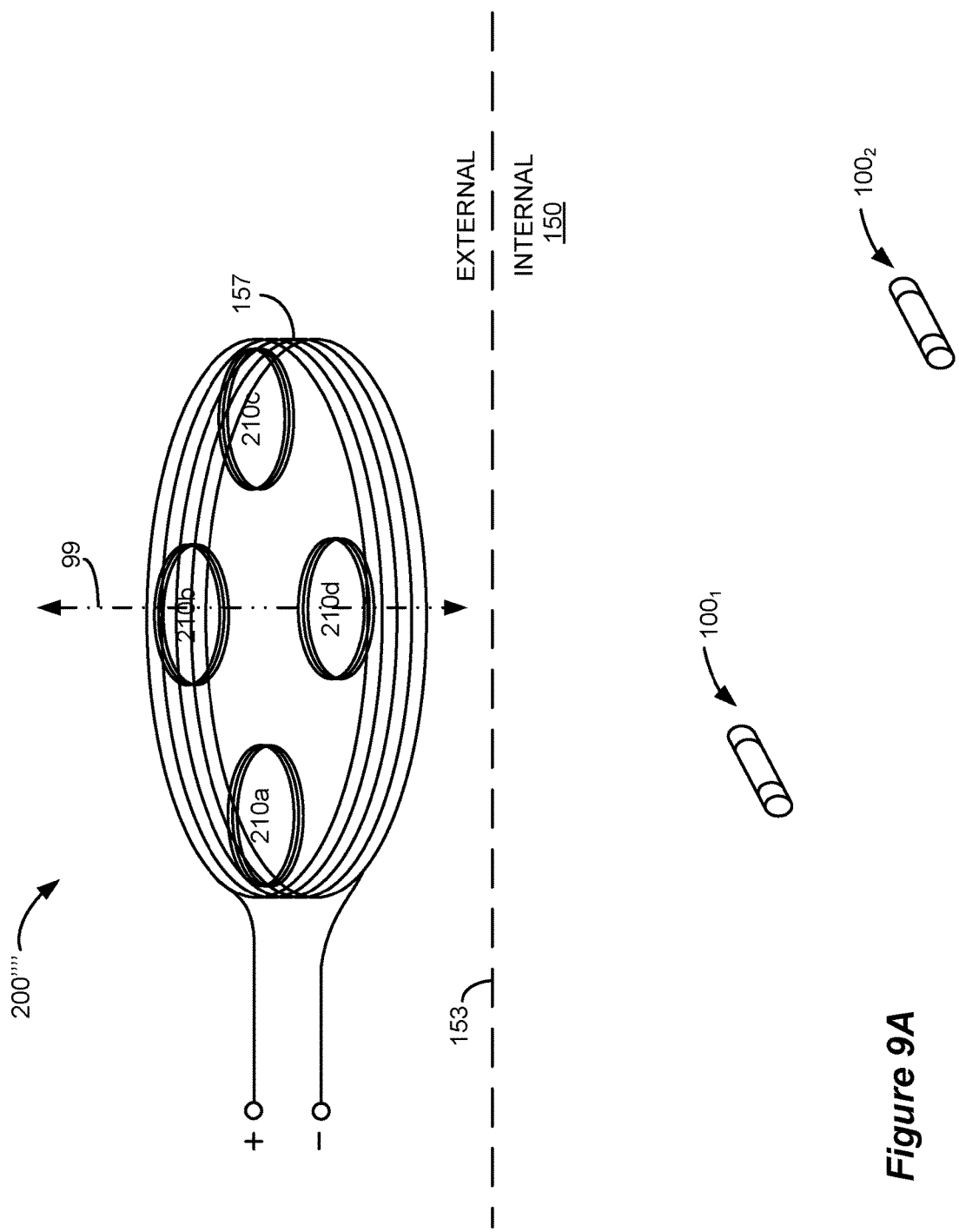
Figure 9C:
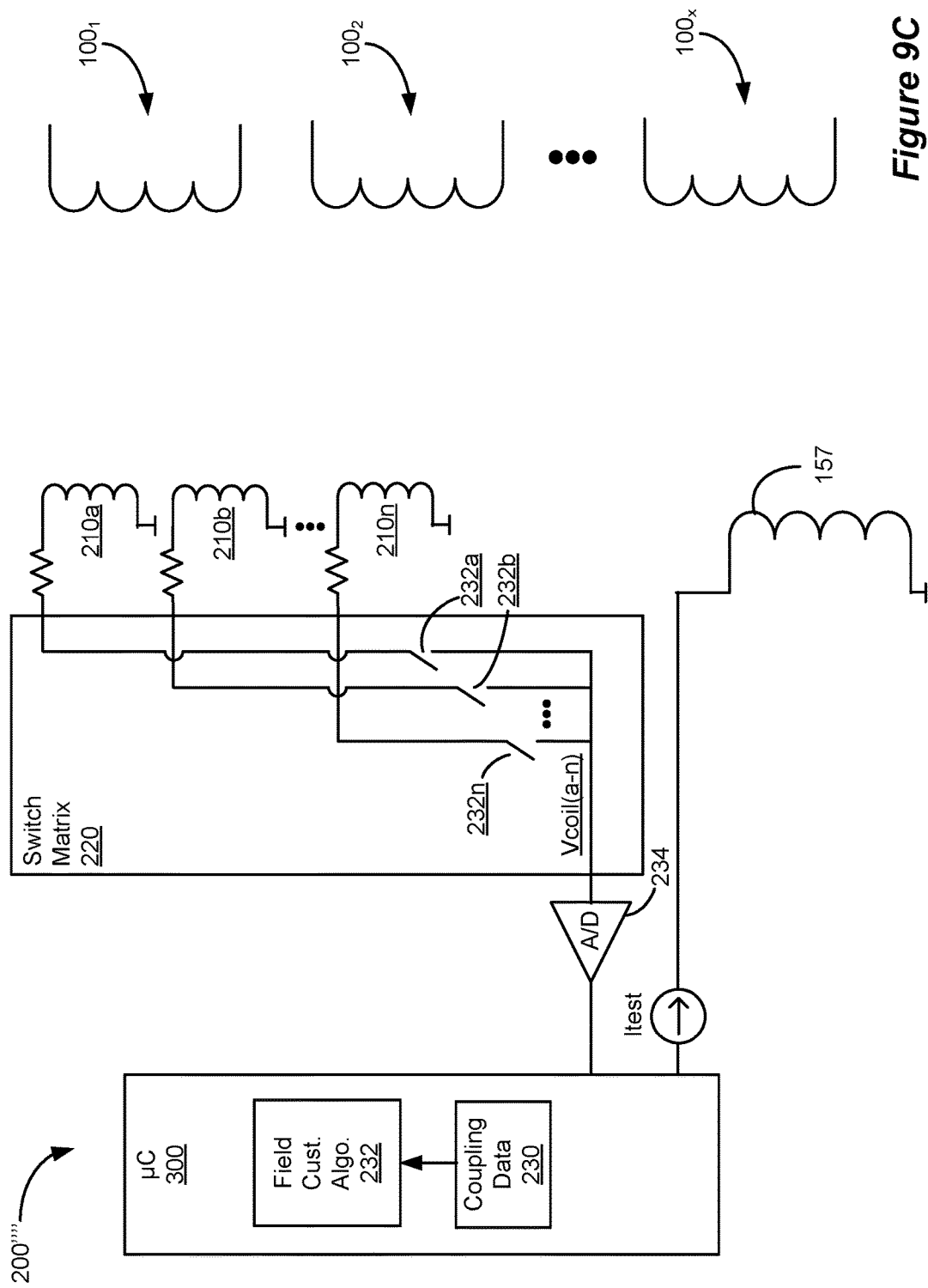

FIGS. 9A-9C illustrate a fifth embodiment of an external charger 200'''' in which coupling to the various microstimulators 100 is measured at the external charger 200'''' without telemetry. As shown, external charger 200'''' once again includes a primary coil 157 and field customization coils 210*a*-*d*, and so is again similar to external charger 200 of FIGS. 5A-5G. And like external charger 200''', external charger 200'''' relies on voltages procured from each of the field customization coils (Vcoil(a-d)) during the testing phase to act as the coupling data 230 used by the field customization algorithm 232 in setting the customization currents Ia-Id during generation of an actual magnetic charging field 201. However, in this instance, the coil voltages, Vcoil(a-d) result from reflections from the microstimulators 100 resulting from a test magnetic field generated by the primary coil 157. As explained, in U.S. patent application Ser. No. 12/498,049, filed Jul. 6, 2009, which is incorporated herein by reference in its entirety, when a test magnetic field reflects off of an microstimulator and is detected at each of the field customization coils 210*a*-*d*, a voltage builds up across the coils, which voltage is smaller at coils 210*a*-*d* that are more strongly coupled to (e.g., are closer to) a microstimulator. As a result, these coil voltages are indicative of the coupling between a given field customization coil 210*a*-*d* and the microstimulator(s), and can used as the coupling 230 data as shown in FIG. 9B. (As with external charger 200''', the Vcoil measurement is not indexed to any particular microcontroller). FIG. 9C shows the circuitry used during the testing phase to procures the Vcoil coupling data 230 in external charger 200''''. Once procured, the coupling data 230 can be used by the field customization algorithm to generate customization currents Ia-Id during an actual charging session, as already described.

Embodiments of the improved external charger to this point have highlighted the utility of simultaneously charging a plurality of microstimulators. However, it should be noted that the improved external chargers can also be of benefit to charging a single microstimulator 100, as is shown in FIGS. 9A-9D. Specifically shown is the use of external charger 200 to charge a single implant, but chargers 200', 200'', and 200''' could be used to the same effect.

Figure 10A:
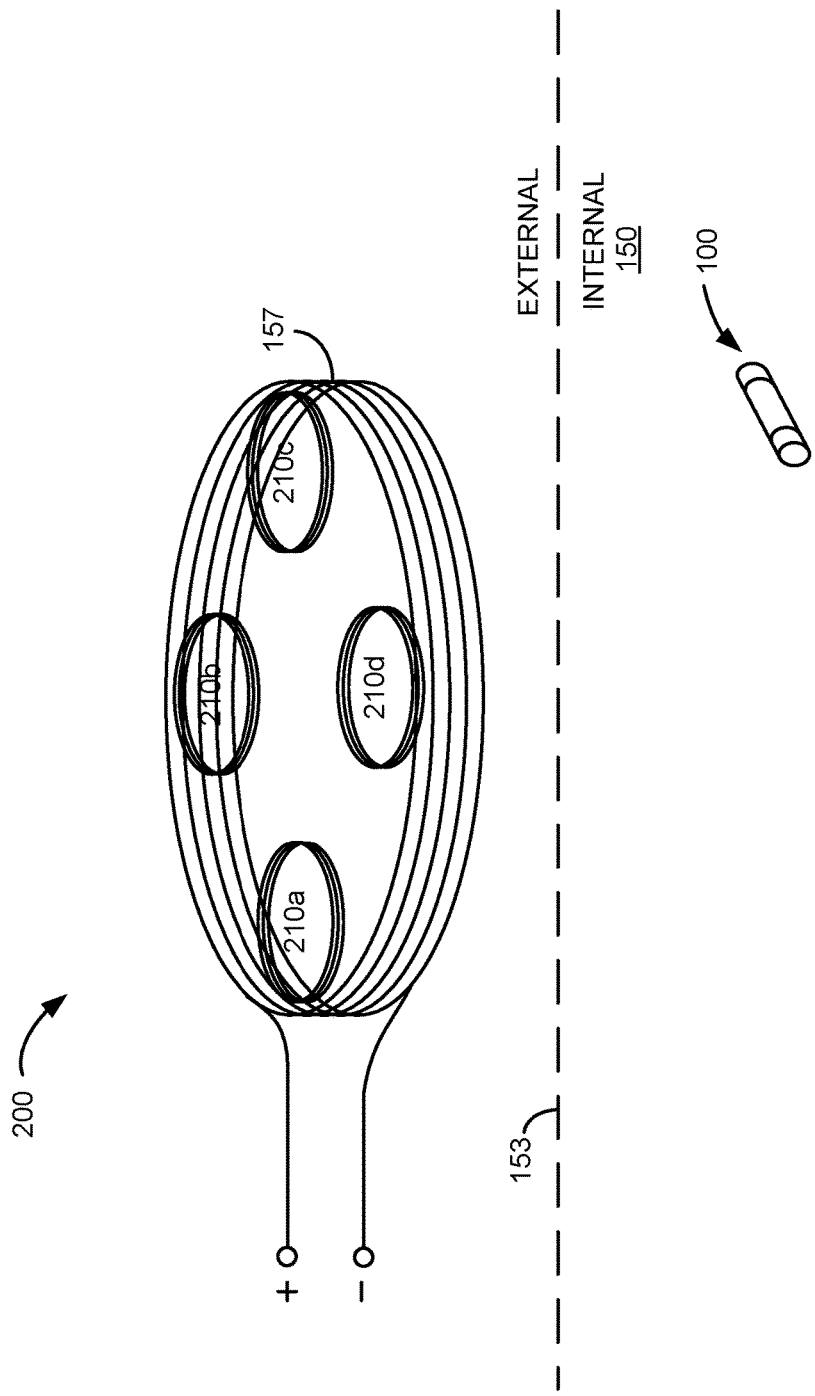
FIGS. 10A-10E illustrate the structure and operation of the improved external chargers as applied to optimization of the charging of a single implantable medical device.
Figure 10B:
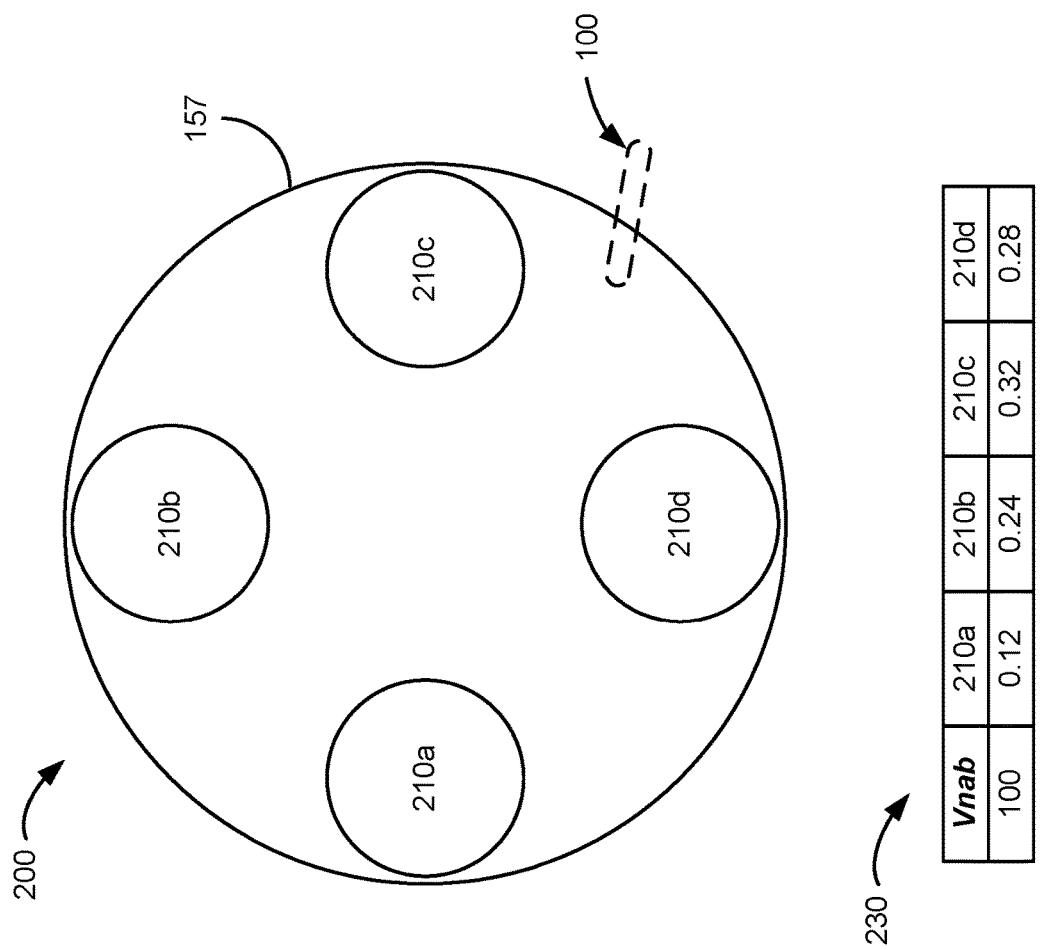
Figure 10C:
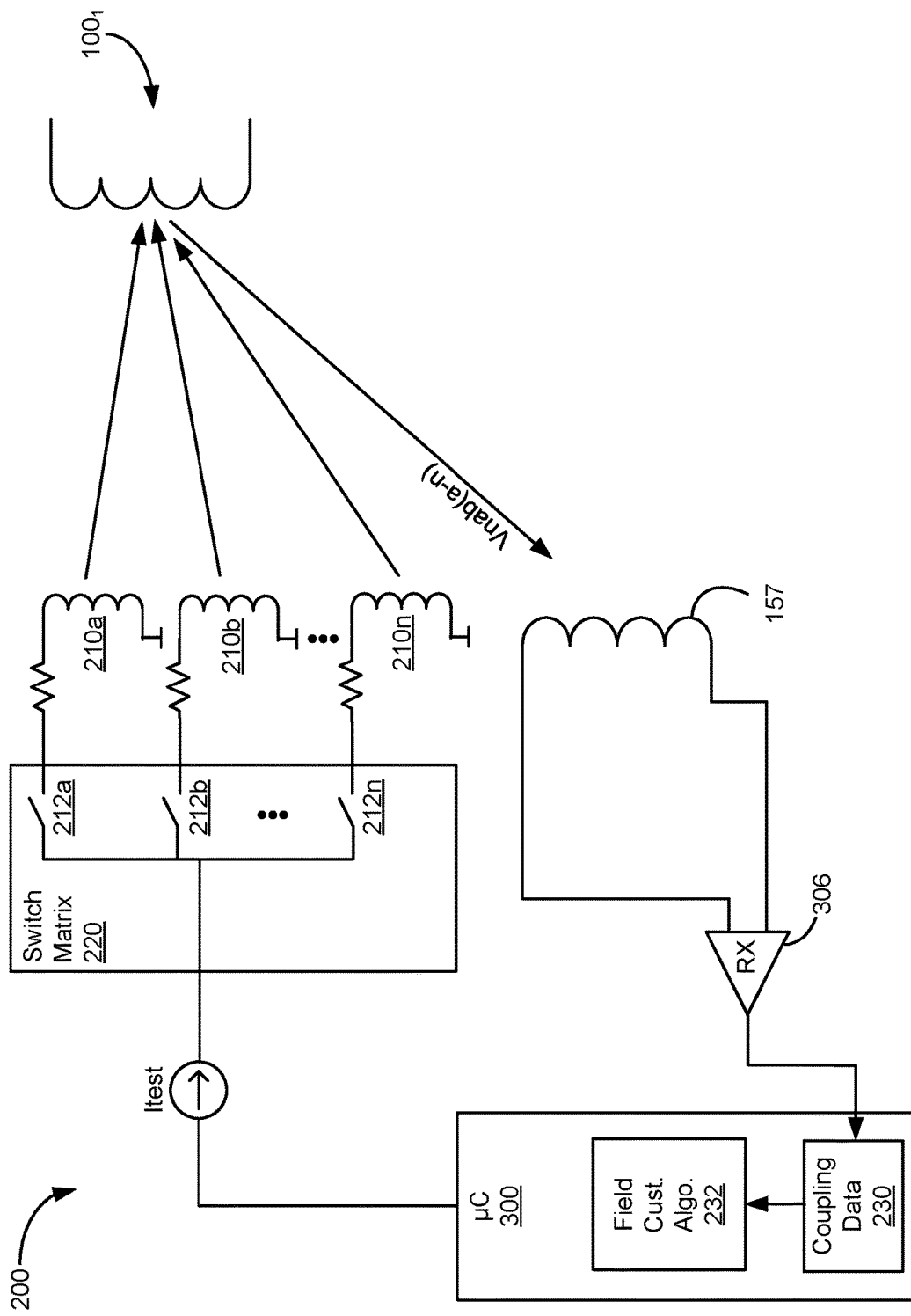
Figure 10D:
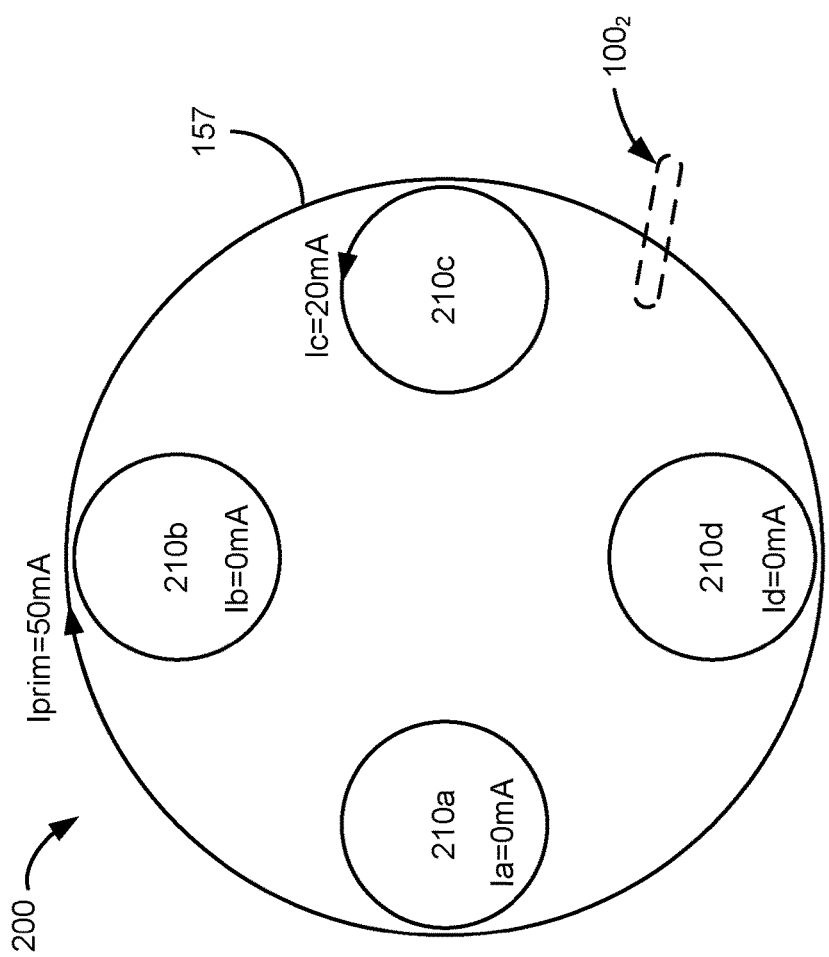

The external charger 200 benefits charging of a single microcontroller by concentrating the magnetic charging field 201 in locations more proximate to the vicinity of the microstimulator 100. This can result, for example, in energy savings in the production of the magnetic charging field 201 because energy may not be spent generating significant fields at locations distant from the microstimulator. For example, in FIG. 10A, note that the external charger 200 is not well-aligned with the microstimulator; it is too far to the left, perhaps as a result of bad placement of the external charger 200 by the patient. As a result, microstimulator 100 is closest to field customization coil 210*c*, a fact which can be verified through a review of the coupling data 230 procured during the testing phase (FIG. 10B). (FIGS. 10B and 10C illustrate use of the telemetered Vnab values as the coupling data 230, but again, Vcoil measurements made at the external charger 200 can also be used). Knowing this, the field customization algorithm 232 can focus energy for the production of the magnetic charging field at field customization coil 210*c*, as shown in FIG. 10D. Notice that the baseline current, Iprim, in the primary coil 157 has been reduced from earlier examples (i.e., from 100 to 50 mA), owing to the fact that a broader generically symmetric magnetic charging field from this coil is not necessary, and is wasteful, given the poor alignment between the external charger 200 and the microstimulator 100. At the same time, field customization coil 210*c* is biased with a customization current Ic which (because it flows in the same direction) reinforces the baseline current, Iprim. In this manner, the overall magnetic charging field 201 produced has its energy concentrated proximately to microstimulator 100, where it can most effectively be used to charge the microstimulator 100.

Figure 10E:
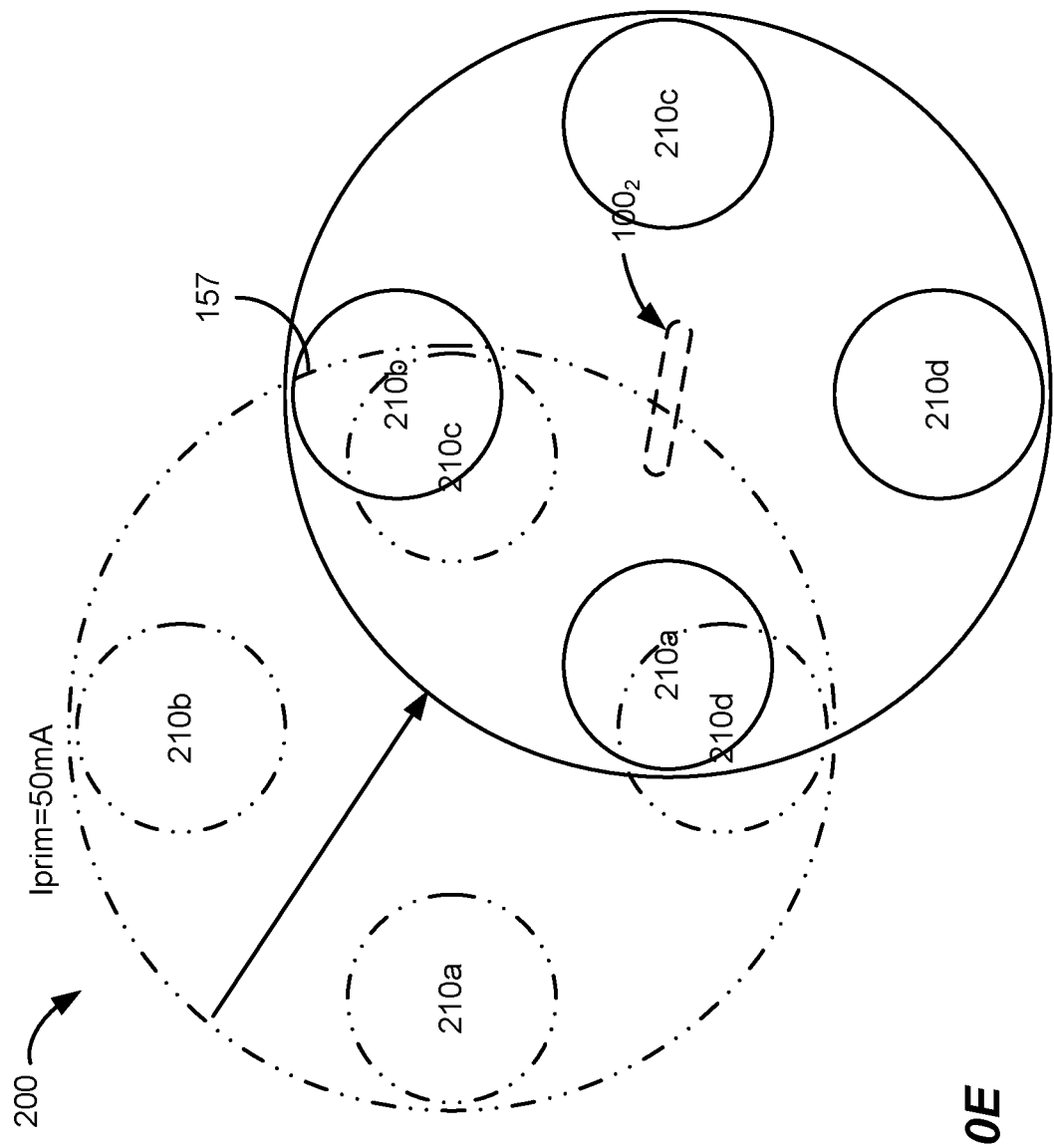

As well as adjusting the generated magnetic charging field, the field customization algorithm 232 can also be used to indicate the alignment between the external charger 200 and the microstimulator 100, which indication can then be used by the patient to better center the external charger 200 over the microstimulator(s), as shown in FIG. 10E. This is explained more fully in U.S. patent application Ser. No.

12/579,740, filed Oct. 15, 2009, which is incorporated herein by reference in its entirety.

"Differently activating" as used herein should be understood to encompass various ways to manipulate the field customization coils to produce a customized magnetic charging field. For example, placing different emphasizing or deemphasizing customization currents in at least some of the field customization coils; coupling at least one of the field customization coils to the primary coil while not coupling others; or opening at least one of the field customization coils while closing others, would comprise examples of situations in which not all of the field customization coils are activated in the same way.

Note that the improved external chargers disclosed herein can be used to charge implantable medical devices even if such devices do not have rechargeable batteries. For example, the external chargers can be used to provide continuous wireless power to implantable medical devices, which devices may directly rectify and use such power without storage, or using only minimal storage means such as capacitors.

The foregoing description related to use of an improved external charger for charging neurostimluators, and in particular microstimulators. However, it is to be understood that the invention is not so limited. Rather, the invention may be used with any type of implantable medical device system that could benefit from improved charging techniques. For example, the present invention may be used as part of a system employing one or more of an implantable sensor, an implantable pump, a pacemaker, a defibrillator, a cochlear stimulator, a retinal stimulator, a spinal cord stimulator, a stimulator configured to produce coordinated limb movement, a cortical and deep brain stimulator, or with any other neural stimulator configured to treat any of a variety of conditions.

While the inventions disclosed have been described by means of specific embodiments and applications thereof, numerous modifications and variations could be made thereto by those skilled in the art without departing from the literal and equivalent scope of the claims set forth herein.

What is claimed is:

1. A method for charging at least one implantable medical device using an external charger comprising a plurality of coils positioned radially symmetrically about a main axis, the method comprising:
differently activating one or more of the plurality of coils in the external charger to create a magnetic charging field that is radially asymmetric with respect to the main axis, wherein the plurality of coils are differently activated in accordance with at least one coupling parameter, wherein each coupling parameter is indicative of the coupling between one of the coils and one implantable medical device.

2. The method of claim 1, further comprising a primary coil centered around the main axis, wherein the primary charging coil is activated as part of creating the magnetic charging field.

3. The method of claim 2, wherein the one or more of the plurality of coils are differently activated by one or more, but not all, of the plurality of coils being coupled in series with the primary coil.

4. The method of claim 1, wherein the one or more of the plurality of coils are differently activated by increasing a current that is supplied to at least one of the plurality of coils to decrease a strength of the magnetic charging field near the at least one of the plurality of coils.

5. The method of claim 1, wherein the one or more of the plurality of coils are differently activated by increasing a current that is supplied to at least one of the plurality of coils to increase a strength of the magnetic charging field near the at least one of the plurality of coils.

6. The method of claim 1, wherein the one or more of the plurality of coils are differently activated by at least one of the plurality of coils carrying a different customization current from the other coils.

7. The method of claim 1, wherein the one or more of the plurality of coils are differently activated by at least one of the plurality of coils, but not all, being closed or opened.

8. The method of claim 1, wherein the coupling parameter for each one of the coils is determined by:
routing a test current through that coil independently; and
measuring a voltage across that coil that is required to support the test current.

9. The method of claim 1, wherein the coupling parameter for each one of the coils is determined by:
routing a test current through that coil independently; and
receiving, via telemetry at the external charger, an indication from the at least one implantable medical device of coupling between that coil and the at least one implantable medical device.

10. The method of claim 1,
wherein the plurality of coils are differently activated in accordance with coupling parameters each indicative of the coupling between one of the coils and the at least one implantable medical device.

11. An external charger for charging at least one implantable medical device, comprising:
a plurality of coils positioned radially symmetrically about a main axis;
wherein one or more of the plurality of coils is configured to be differently activated to create a magnetic charging field that is radially asymmetric with respect to the main axis, and
wherein the different activation of one or more of the plurality of coils is configured to occur in accordance with at least one coupling parameter, wherein each coupling parameter is indicative of the coupling between one of the coils and one implantable medical device.

12. The external charger of claim 11, further comprising a primary coil centered around the main axis, wherein the primary charging coil is configured to be activated as part of creating the magnetic charging field.

13. The external charger of claim 12, wherein the one or more of the plurality of coils are configured to be differently activated by one or more, but not all, of the plurality of coils being coupled in series with the primary coil.

14. The external charger of claim 11, wherein the one or more of the plurality of coils are configured to be differently activated by increasing a current that is supplied to at least one of the plurality of coils to decrease a strength of the magnetic charging field near the at least one of the plurality of coils.

15. The external charger of claim 11, wherein the one or more of the plurality of coils are configured to be differently activated by increasing a current that is supplied to at least one of the plurality of coils to increase a strength of the magnetic charging field near the at least one of the plurality of coils.

16. The external charger of claim 11, wherein the one or more of the plurality of coils are configured to be differently activated by at least one of the plurality of coils carrying a different customization current from the other coils.

17. The external charger of claim 11, wherein the one or more of the plurality of coils are configured to be differently activated by at least one of the plurality of coils, but not all, being closed or opened.

18. The external charger of claim 11, wherein the coupling parameter for each one of the coils is configured to be determined by:
routing a test current through that coil independently; and
measuring a voltage across that coil that is required to support the test current.

19. The external charger of claim 11, wherein the coupling parameter for each one of the coils is configured to be determined by:
routing a test current through that coil independently; and
receiving, via telemetry at the external charger, an indication from the at least one implantable medical device of coupling between that coil and the at least one implantable medical device.

20. The external charger of claim 11, wherein the different activation of one or more of the plurality of coils is configured to occur in accordance with coupling parameters, wherein each coupling parameter is indicative of the coupling between one of the coils and one implantable medical device.

\* \* \* \* \*